(12) United States Patent
Huang

(10) Patent No.: US 7,982,030 B2
(45) Date of Patent: Jul. 19, 2011

(54) SYNTHESIS OF SELENIUM-DERIVATIZED NUCLEOSIDES, NUCLEOTIDES, PHOSPHORAMIDITES, TRIPHOSPHATES AND NUCLEIC ACIDS

(75) Inventor: Zhen Huang, Marietta, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 0 days.

(21) Appl. No.: 12/562,960

(22) Filed: Sep. 18, 2009

(65) Prior Publication Data

US 2010/0137573 A1 Jun. 3, 2010

Related U.S. Application Data

(62) Division of application No. 10/104,995, filed on Mar. 22, 2002, now Pat. No. 7,592,446.

(60) Provisional application No. 60/277,830, filed on Mar. 22, 2001.

(51) Int. Cl.
| | |
|---|---|
| C07H 19/173 | (2006.01) |
| C07H 21/04 | (2006.01) |
| C07H 19/00 | (2006.01) |
| C07D 239/46 | (2006.01) |
| C07D 421/04 | (2006.01) |
| A61K 31/506 | (2006.01) |
| A61P 48/00 | (2006.01) |

(52) U.S. Cl. .................. 536/27.21; 514/263.1; 544/264; 536/27.6; 536/27.81; 536/25.3; 536/28.54

(58) Field of Classification Search .................. 544/264; 536/27.21, 27.6, 27.81; 514/263.1
See application file for complete search history.

(56) References Cited

U.S. PATENT DOCUMENTS

| | | | | |
|---|---|---|---|---|
| 3,998,806 | A | * | 12/1976 | Townsend .................. 536/27.81 |
| 4,536,571 | A | * | 8/1985 | Stockel et al. .............. 536/27.81 |
| 4,552,955 | A | * | 11/1985 | Takaku et al. ............... 536/27.14 |
| 4,617,189 | A | * | 10/1986 | Stockel et al. ................. 424/702 |
| 5,166,330 | A | * | 11/1992 | Engels et al. ................. 536/26.3 |
| 5,359,052 | A | * | 10/1994 | Stee et al. ..................... 536/26.7 |
| 5,449,664 | A | * | 9/1995 | Verheyden et al. ............. 514/45 |
| 5,512,668 | A | * | 4/1996 | Stec et al. .................... 536/25.33 |
| 5,700,660 | A | | 12/1997 | Leonard et al. |
| 5,856,465 | A | * | 1/1999 | Stec et al. ..................... 536/25.3 |
| 5,883,237 | A | | 3/1999 | Stec et al. |
| 6,348,583 | B1 | | 2/2002 | Segev |

FOREIGN PATENT DOCUMENTS

WO WO 98/49179 11/1998

OTHER PUBLICATIONS

Mautner et al. J. Med. Chem. 6, 36-39, 1963.*
Chu et al. J. Med. Chem. 18, 559-564, 1975( Chu-1).*
Chu et al. J. Med. Chem. 17, 406-409, 1974( Chu-2).*
Adrian R. Ferré-D' Amaré, Kaihong Zhou and Jennifer A. Doudna, "Crystal structure of a hepatitis delta virus-ribozyme," *Nature* (1998) 395:567-574.
Bollmark et al., Chemical Communications, 11, 991-992, 1997; CA 127:95522, 1997.
Choi et al., Journal of Medicinal Chemistry, 22(6), 618-621, 1979.
Helinski et al., Nucleosides & Nucleotides, 12(16), 597-604, 1993; CA 120: 31143, 1994.
Helinski et al., Phosphorous, Sulfur and Silicon and related Elements, 76(1-4), 395-398, 1993; CA 120: 192167, 1994.
Nemer et al., Tetrahedron Letters, 106(20), 21(43), 4153-4154, 1980.
Nemer et al., Tetrahedron Letters, 21(43), 4149-4152, 1980.
Quan Du, Nicolas Carrasco, Marianna Teplova, Christopher J. Wilds, Martin Egli, and Zhen Huang, "Internal Derivatization of Oligonucleotides with Selenium for X-ray Crystallography Using MAD", *J. Am. Chem. Soc.* (2002) 124: 24-25.
Sekine et al., Chemistry Letters, (7), 801-802, 1979.
Shih-His Chu, Chyng-Yann Shiue, and Ming-Yu Chu, "Synthesis and Biological Activity of Some 8-Substituted Selenoguanosine Cyclic 3',5'-Phosphates and Related Compounds," *Journal of Medicinal Chemistry* (1975) 18: 559-564.
Stawinski et al., Tetrahedron Letters, 30(16), 2157-2160, 1989.
Stawinski et al., Tetrahedron Letters, 33(47), 7255-7258, 1992.
Stec et al., Journal of American Chemical Society, 106(20), 6077-66079, 1984.
Wei-Mei Ching, Birgit Alzner-DeWeerd, and Thressa C. Stadtman, "A selenium-containing nucleoside at the first position of the anticodon in seleno-tRNA$^{Glu}$ from *Clostridium stricklandii*," *Proc. Natl. Acad. Sci. USA* (1985) 82: 347-350.
Wozniak et al., Bioorganic & Medicinal Chemistry Letters, 4(8), 1033-1036, 1994.
Zsuzsa Veres, Lin Tsai, Thomas D. Scholz, Michael Zpolitino, Robert S. Balaban, and Thressa C. Stadtman, "Synthesis of 5-methylaminomethyl-2-selenouridine in tRNAs: $^{31}$P NMR studies show the liable selenium donor synthesized by the *se*/D gene product contains selenium bonded to phosphorus," *Proc. Natl. Acad. Sci. USA* (1992) 89: 2975-2979.

* cited by examiner

*Primary Examiner* — Venkataraman Balasubramanian
(74) *Attorney, Agent, or Firm* — Sutherland Asbill & Brennan LLP

(57) ABSTRACT

The present invention provides selenium derivatives of nucleosides, nucleoside phosphoramidites, nucleotides, nucleotide triphosphates, oligonucleotides, polynucleotides, and larger nucleic acids and methods for their synthesis. Selenium derivatives of both ribonucleic acids and deoxyribonucleic acids, as well as methods for their synthesis, crystallization and uses in structural determinations, particularly by X-ray crystallographic techniques are disclosed. The selenium derivatives of the present invention are also useful as food supplements.

17 Claims, 11 Drawing Sheets

OTBDMS: *tert*-butyldimethylsilyloxyl

DMTr = dimethoxytrityl
TBDMS = *tert*-butyldimethylsilyl
Ms = methanesulfonate

Partial MS spectrum of 2'-methyl-seleno-5'-DMTr-uridine by positive electrospray in an $NH_3$-$NH_4^+$ buffer.

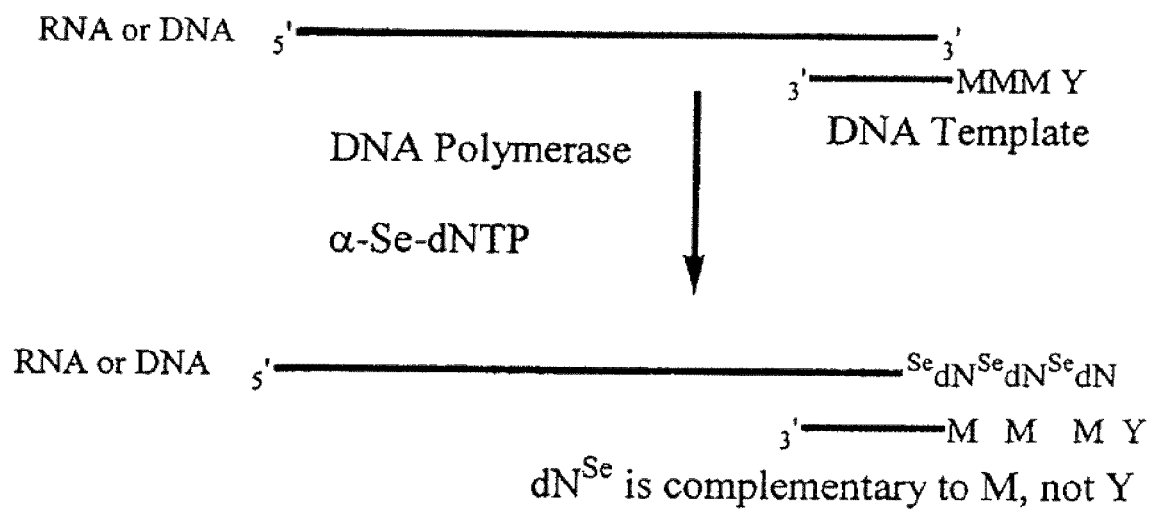
Figure 9 Terminal Extension of RNAs and DNAs using α-Se-dNTPs

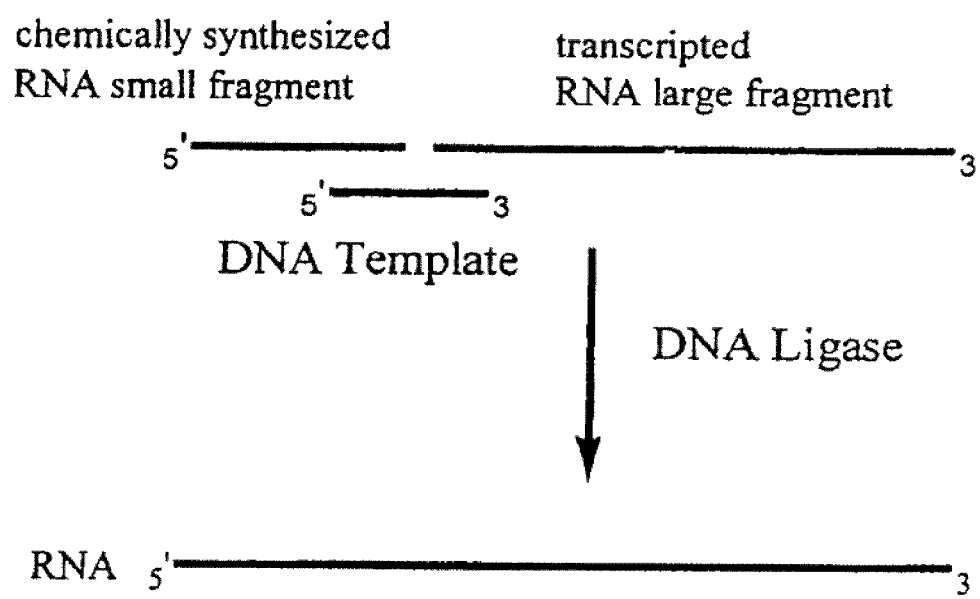
Figure 10 Ligation of RNA Fragments on a DNA Template

SEQUENCE LISTING

```
<160> NUMBER OF SEQ ID NOS: 3

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: 2'-methylseleno-thymine

<400> SEQUENCE: 1
gcgtatacgc                                                          10

<210> SEQ ID NO 2
<211> LENGTH: 10
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-methylseleno-uridine

<400> SEQUENCE: 2
gcgtauacgc                                                              10

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gcgtatacgc                                                              10
```

SYNTHESIS OF SELENIUM-DERIVATIZED NUCLEOSIDES, NUCLEOTIDES, PHOSPHORAMIDITES, TRIPHOSPHATES AND NUCLEIC ACIDS

RELATED APPLICATIONS

The present application is a divisional of U.S. patent application Ser. No. 10/104,995, filed Mar. 22, 2002, now U.S. Pat. No. 7,592,446, which claims the benefit of provisional application No. 60/277,830, filed Mar. 22, 2001, both of which are incorporated herein by reference in their entireties.

SEQUENCE LISTING

The instant application contains a Sequence Listing which has been submitted via EFS-Web and is hereby incorporated by referenced in its entirety. Said ASCII copy, created on Feb. 8, 2010, is named 13100027.txt, and is 1,331 bytes in size.

BACKGROUND

Determination of the three-dimensional structures of RNA molecules, RNA-protein and DNA-protein complexes with high resolution is invaluable for gaining understanding of biological systems at the molecular level. (See for example, refs. 1-4). X-ray crystallography is the most direct and powerful tool for structure determination of these macromolecules. (Refs. 5-7). However, derivatization with heavy atoms for phase determination, a long-standing problem in nucleic acid X-ray crystallography, has impeded the structural determination process. (Refs. 8, 9). It can take years just to prepare derivatives and to determine the required phase information using traditional approaches.

Currently, derivatization approaches include heavy-atom soaking of crystals, co-crystallization, and halogen-derivatization of oligonucleotides. Heavy-atom soaking and co-crystallization have proven to be much more difficult for nucleic acids than for proteins, probably because nucleic acids lack specific metal ion binding sites. 5-halogen-uridine (5-bromine or iodine) or 5-halogen-deoxyuridine (thymidine mimic) is used to derivatize nucleic acids for phase determination. As these halogenated nucleotides are not very stable under X-ray or UV irradiation, long exposure may cause decomposition. (Ref. 10). In the case of iodine derivatives, isomorphism is a requirement for the Multiple Isomorphous Replacement (MIR) technique, but crystal structures of iodine derivatives not always isomorphous with (i.e. do not adopt the same molecular conformation as) the native structures, (see for example, Refs. 9 and 11) which limits the usefulness of the iodine derivatives in structural determination.

The Multiwavelength Anomalous Dispersion (MAD) technique has been developed for structure determination of macromolecules using synchrotron and anomalous scattering atoms. (Refs. 12 and 14). The synchrotron radiation provides the required X-ray wavelengths, and anomalous scatterers, such as selenium or bromine, can provide distinctive diffraction pattern for phase determination. As phasing signal of bromine is relatively weaker than that of selenium, more bromine atoms need to be incorporated into large nucleic acid molecules in order to successfully use MAD phasing. Incorporation of many bromine atoms, with limited choice of positioning, can cause significant changes in native structures. (Refs. 9 and 11). Bromine derivatives, used in current MAD phasing, are thereby more limited to structure determination of small oligonucleotides.

Another problem with bromine derivatives is the limited choice of positioning, and even where substitution is possible, structural perturbation is difficult to avoid. (Refs. 9, 11). Therefore, there is a need for alternative derivatives that require incorporation of a few heavy atoms, and allow choice of heavy atom positioning to avoid structural perturbation, which is especially important for labeling large nucleic acid molecules for MAD phasing.

Nucleic acids (Designated as structure 1 in FIG. 1) may be prepared by solid-phase synthesis using phosphoramidites (Structure 2), in vitro RNA transcription or DNA polymerization using triphosphates (Structure 3) as building blocks according to well known methods. See for example, Gait, M. J. (1991) DNA/RNA synthesis and labeling, *Curr. Opin Biotechnol.* 2(1): 61-68; and Sproat, B. S. (1995) Chemistry and applications of oligonucleotide analogues, *J. Biotechnol.* 41(2-3): 221-238.

There is a need for methods whereby any one of the oxygen atoms of a nucleotide unit, including 2', 3', 5', and α-phosphate oxygen atoms, the ring oxygen atom, and oxygen atoms of the nucleobases, may be selectively replaced by selenium. Such methods would be particularly valuable in offering a choice for positioning selenium atoms, especially if this could be achieved without structural perturbation in nucleic acids. These molecules would then be useful for determinations of the native structures without the Selenium modification.

Selenium is an essential trace element for humans. Statistic data and survey indicate that people die from lack of selenium in some parts of the world. Though a limited amount of research has addressed the metabolism of selenium in humans, much is known about how experimental animals regulate selenium. It is reported that selenium deficiency increases the pathology of an influenza virus infection. Beck, M. A.; Nelson, H. K.; Shi, Q.; Van Dael, P.; Schiffrin, E. J.; Blum, S.; Barclay, D.; Levander, O. A., "Selenium deficiency increases the pathology of an influenza virus infection", *J. FASEB* 2001, 15, 1481-1483.

In a mouse model, it was also observed that a benign strain of coxsackievirus B3 became virulent and caused myocarditis in selenium- and vitamin E-deficient mice. Beck, M. A.; Levander, O. A., "Host nutritional status and its effect on a viral pathogen", *J. Infect Dis.* 2000, 182 Suppl 1:S93-96. This change in pathogenicity was due to mutations in the viral genome, which changed an avirulent virus into a virulent one. Once these mutations occurred, even mice with normal nutriture developed disease from the mutated virus.

These results suggest that the oxidative stress status and selenium level of the host can have a profound influence on a viral pathogen. Pathogenesis of mycobacterial disease in HIV-infected people is also influenced by selenium status. Shor-Posner, G.; Miguez, M. J.; Pineda, L. M.; Rodriguez, A.; Ruiz, P.; Castillo, G.; Burbano, X.; Lecusay, R.; Baum, M., "Impact of selenium status on the pathogenesis of mycobacterial disease in HIV-1-infected drug users during the era of highly active antiretroviral therapy", *J Acquir Immunme Defic Syndr* 2002, 29, 169-173.

Selenium supplementation has been reported to suppress carcinogenesis in many animal models. Finley, J. W; Ip, C.; Lisk, D. J.; Davis, C. D.; Hintze, K, J.; Whanger, P. D., "Cancer-Protective Properties of High-Selenium Broccoli', *J. Agric. Food Chem.* 2001, 49, 2679-2683. The cancer protective effect of dietary selenium in humans is also supported by intervention trials as well as by epidemiological data. Manar, M. J.; MacPherson, G. D.; Mcardle, F.; Jackson, M. J.; Hart, C. A., "Selenium status, kwashiorkor and congestive heart failure", *Acta Paediatr* 2001, 90, 950-952.

Hence, there is a need for selenium nucleoside, selenium nucleotides and selenium derivatives of nucleic acids as food supplements. Such selenium derivatives would be valuable as anticancer agents.

SUMMARY OF THE INVENTION

In one aspect, the present invention provides a selenium-containing analog of a nucleoside, a nucleotide, a nucleotide phosphoramidite, an oligonucleotide or a nucleic acid having the structure of formula I:

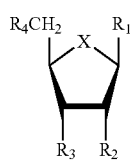

(Formula I)

in which: (a) $R_1$ is a nucleic acid base selected from adenine, 8-selenoadenine, thymine, 2-selenothymine, 4-selenothymine, uracil, 4-selenouracil, guanine, 6-selenoguanine, cytosine and 2-selenocytosine; or is a protected nucleic acid base selected from adenine, 8-selenoadenine, thymine, 2-selenothymine, 4-selenothymine, uracil, 4-selenouracil, guanine, 6-selenoguanine, cytosine and 2-selenocytosine;

(b) $R_2$ is H, HO, alkyl-O, orthoester, TBDMS-O, HSe, diselenide, alkyl-Se;

(c) $R_3$ is H, HO, alkyl-O, TBDMS-O, HSe, diselenide, alkyl-Se, phosphoramidite, phosphoroselenoamidite, phosphate, phosphoroselenoate, a 5' linked nucleotide, a 5' linked seleno-nucleotide, a 5' linked oligonucleotide, a 5' linked seleno-oligonucleotide, a 5' linked nucleic acid chain or a 5' linked seleno-nucleic acid chain;

(d) $R_4$ is H, HO, alkyl-O, TBDMS-O, HSe, diselenide, alkyl-Se, DMTr-O, phosphate, phosphoroselenoate, diphosphate, diphosphoroselenoate, triphosphate, triphosphoroselenoate, a 3' linked nucleotide, a 3' linked oligonucleotide, a 3' linked nucleotide, a 3' linked oligonucleotide or a nucleic acid chain; and (e) X is an oxygen atom or a selenium atom; and
wherein at least one of $R_1$, $R_2$, $R_3$, $R_4$ or X comprises at least one selenium atom, and wherein alkyl is a saturated or unsaturated, branched or unbranched hydrocarbon group having between 1 and 24 carbon atoms.

In another aspect, the invention provides a process for preparing a compound having the structure of formula I:

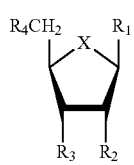

(Formula I)

in which: (a) $R_1$ is a nucleic acid base selected from adenine, 8-selenoadenine, thymine, 2-selenothymine, 4-selenothymine, uracil, 4-selenouracil, guanine, 6-selenoguanine, cytosine and 2-selenocytosine; or $R_1$ is a protected nucleic acid base selected from adenine, 8-selenoadenine, thymine, 2-selenothymine, 4-selenothymine, uracil, 4-selenouracil, guanine, 6-selenoguanine, cytosine and 2-selenocytosine;

(b) $R_2$ is H, HO, alkyl-O, orthoester, TBDMS-O, or Z;

(c) $R_3$ is H, HO, alkyl-O, TBDMS-O, phosphoramidite, phosphate or Z;

(d) $R_4$ is H, HO, alkyl-O, TBDMS-O, OSi(O-alkyl)$_3$, DMTr-O, phosphate, diphosphate, triphosphate or Z; and (e) X is an oxygen atom or a selenium atom; and
wherein at least one of $R_2$, $R_3$, $R_4$ comprises at least one selenium atom; and wherein Z is HSe, diselenide, alkyl-Se, phosphoroselenoamidite, or phosphoroselenoate; wherein alkyl is a saturated or unsaturated, branched or unbranched hydrocarbon group having between 1 and 24 carbon atoms; and wherein at least one of $R_2$, $R_3$, or $R_4$ is Z;
the process includes:
providing a precursor, the precursor having the structure of the compound except that Z is a leaving group; and reacting the precursor with a selenide ion or an alkyl selenide ion.

In a further aspect, the present invention provides a process for preparing a selenium derivative of a nucleic acid, comprising:
I. providing an immobilized 5'-3' oligonucleotide or an immobilized nucleic acid chain; and
II. providing a selenium-containing activated nucleotide precursor having the structure of formula I:

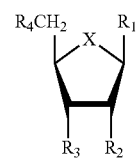

(Formula I)

in which: (a) $R_1$ is a nucleic acid base selected from adenine, 8-selenoadenine, thymine, 2-selenothymine, 4-selenothymine, uracil, 4-selenouracil, guanine, 6-selenoguanine, cytosine and 2-selenocytosine; or $R_1$ is a protected nucleic acid base selected from adenine, 8-selenoadenine, thymine, 2-selenothymine, 4-selenothymine, uracil, 4-selenouracil, guanine, 6-selenoguanine, cytosine and 2-selenocytosine;

(b) $R_2$ is H, HO, alkyl-O, orthoester, TBDMS-O, HSe, diselenide, alkyl-Se;

(c) $R_3$ is H, HO, alkyl-O, TBDMS-O, HSe, diselenide, alkyl-Se having an alkyl, phosphoramidite, phosphoroselenoamidite, phosphate, phosphoroselenoate, a 5' linked nucleotide, a 5' linked seleno-nucleotide, a 5' linked oligonucleotide, 5' linked seleno-oligonucleotide, a 5' linked nucleic acid chain or a 5' linked seleno-nucleic acid chain;

(d) $R_4$ is H, HO, HSe, diselenide, alkyl-Se, DMTr-O, TBDMS-O, phosphate, phosphoroselenoate, diphosphate, diphosphoroselenoate, triphosphate, or triphosphoroselenoate; and (e) X is an oxygen atom or a selenium atom; and
wherein at least one of $R_1$, $R_2$, $R_3$, $R_4$ or X comprises at least one selenium atom, and wherein alkyl is a saturated or unsaturated, branched or unbranched hydrocarbon group having between 1 and 24 carbon atoms; and $R_3$ or $R_4$ comprises an activating group;
III. contacting the immobilized 5'-3' oligonucleotide or the 5'-3' immobilized nucleic acid chain with the selenium-containing activated nucleotide precursor under conditions suitable for addition of the activated nucleotide precursor to the immobilized 5'-3' oligonucleotide or the immobilized 5'-3' nucleic acid chain.

In yet another aspect, the invention provides a process for preparing a selenium derivative of a nucleic acid, comprising:
I. providing an enzyme capable of adding to nucleotide or oligonucleotide into an oligonucleotide or a nucleic acid chain;
II. providing a nucleotide or oligonucleotide substrate of the enzyme and a selenium-containing nucleotide or a selenium-containing oligonucleotide or a selenium-containing nucleic acid chain of the formula I:

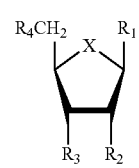

(Formula I)

in which: (a) $R_1$ is a nucleic acid base selected from adenine, 8-selenoadenine, thymine, 2-selenothymine, 4-selenothymine, uracil, 4-selenouracil, guanine, 6-selenoguanine, cytosine and 2-selenocytosine;

(b) $R_2$ is H, HO, alkyl-O, TBDMS-O, HSe, diselenide, alkyl-Se;

(c) $R_3$ is H, HO, alkyl-O, TBDMS-O, HSe, diselenide, alkyl-Se, phosphoramidite, phosphoroselenoamidite, phosphate, phosphoroselenoate, a 5' linked nucleotide, a 5' linked seleno-nucleotide, a 5' linked oligonucleotide, 5' linked seleno-oligonucleotide, a 5' linked nucleic acid chain or a 5' linked seleno-nucleic acid chain;

(d) $R_4$ is H, HO, alkyl-O, TBDMS-O, HSe, diselenide, alkyl-Se, phosphoramidite, phosphoroselenoamidite, phosphoroselenoate, phosphate, diphosphate, diphosphoroselenoate, triphosphate, triphosphoroselenoate, a 3' linked nucleotide, a 3' linked oligonucleotide or a 3' linked nucleic acid chain; and (e) X is an oxygen atom or a selenium atom; and wherein at least one of $R_1$, $R_2$, $R_3$, $R_4$ or X comprises at least one selenium atom and wherein alkyl is a saturated or unsaturated, branched or unbranched hydrocarbon group having between 1 and 24 carbon atoms;

III. contacting the enzyme with the substrate and the selenium-containing nucleotide or selenium-containing oligonucleotide of formula I under conditions suitable for addition of the selenium-containing nucleotide or the selenium-containing oligonucleotide to the substrate.

In a yet further aspect, the invention provides a food supplement comprising a selenium-containing analog of a nucleoside, a nucleotide, an oligonucleotide or a nucleic acid of the structure of formula I:

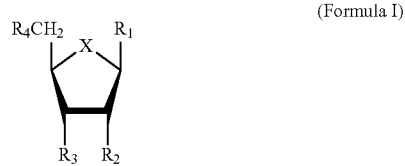

(Formula I)

in which:

(a) $R_1$ is a nucleic acid base selected from adenine, 8-selenoadenine, thymine, 2-selenothymine, 4-selenothymine, uracil, 4-selenouracil, guanine, 6-selenoguanine, cytosine and 2-selenocytosine;

(b) $R_2$ is H, HO, alkyl-O, TBDMS-O, orthoester, HSe, diselenide, alkyl-Se;

(c) $R_3$ is H, HO, alkyl-O, TBDMS-O, HSe, diselenide, alkyl-Se, phosphate, phosphoroselenoate, a 5' linked nucleotide, a 5' linked seleno-nucleotide a 5' linked oligonucleotide, 5' linked seleno-oligonucleotide, a 5' linked nucleic acid chain or a 5' linked seleno-nucleic acid chain;

(d) $R_4$ is H, HO, TBDMS-O, HSe, diselenide, alkyl-Se, phosphate, phosphoroselenoate, diphosphate, diphosphoroselenoate, triphosphate, triphosphoroselenoate, a 3' linked nucleotide, a 3' linked oligonucleotide or a nucleic acid chain; and (e) X is an oxygen atom or a selenium atom; and wherein at least one of $R_1$, $R_2$, $R_3$, $R_4$ or X comprises at least one selenium atom, and wherein alkyl is a saturated or unsaturated, branched or unbranched hydrocarbon group having between 1 and 24 carbon atoms.

BRIEF DESCRIPTION OF THE FIGURES

FIG. 9: Enzymatic terminal extension of RNAs and DNAs using α-SE-NTPs or α-SE-dNTPs.

FIG. 10: Ligation of RNA fragments on a DNA template.

DETAILED DESCRIPTION OF THE INVENTION

Figure 1:
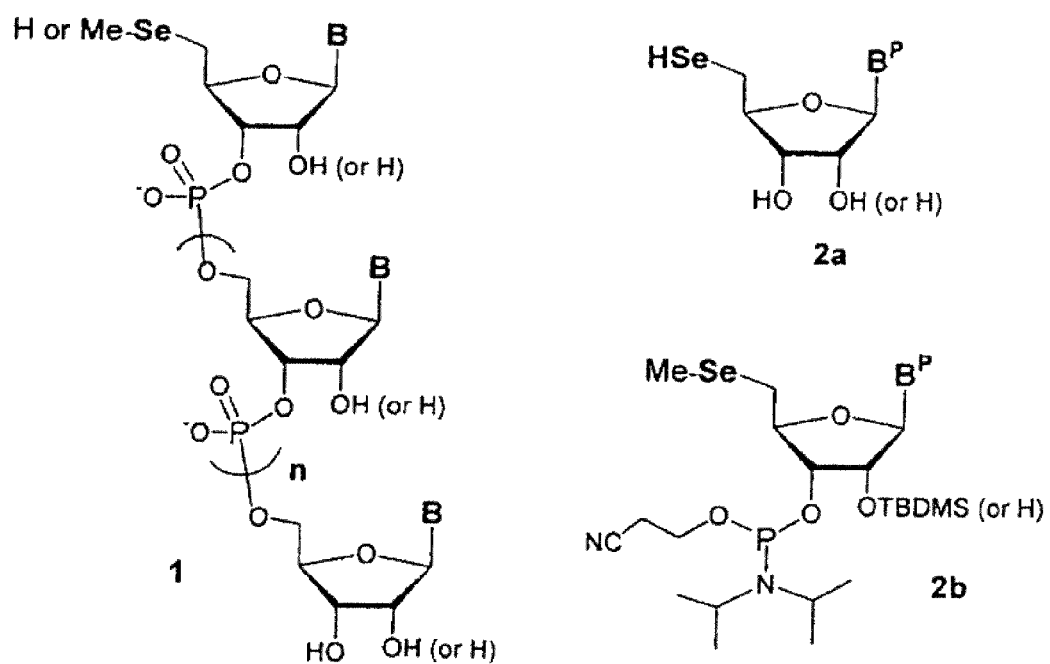
FIG. 1. Formula 1: Nucleic acid chain showing position of 5' MeSe substitution. Formula 2a: 5' Se derivative of a nucleoside with a protected base $B^P$ and 2' OH (ribonucleotide) or 2' H (deoxyribonucleotide). Formula 2b: 5' MeSe derivative of a nucleoside with a protected base $B^P$ and optional O-TBDMS or H at the 2' position and 3' phosphoramidite activating group.

The present invention provides selenium derivatives of nucleosides, nucleotides, nucleotide phosphoramidites, nucleotide triphosphates, oligonucleotides, polynucleotides, and larger nucleic acids, both ribonucleic acids and deoxyribonucleic acids. Also provided are methods for their synthesis and crystallization for use in structural determinations, particularly by X-ray crystallographic techniques.

The present invention relates to selenium-containing analogs of a nucleoside, a nucleotide, a nucleotide phosphoramidite, an oligonucleotide or a nucleic acid. For convenience, these selenium-containing analogs are hereinafter referred to as the selenium derivatives of the present invention.

The selenium derivatives of the present invention include one or more selenium atoms or selenium-containing groups. The selenium-containing group may be any selenium-containing group, such as for instance, HSe, or alkyl-Se. The alkyl-Se groups may be any alkyl-Se groups, such as for example, methyl-Se, ethyl-Se or propyl-Se, although longer chain lengths up to about 18 or even 24 carbon atoms in length are also contemplated. The alkyl chain may be branched or straight chain, saturated or unsaturated, with one or more double and/or triple bonds at any position, at an end or within the chain.

Other examples of selenium-containing groups useful in practicing the present invention include selenide, alkylselenides, such as methylselenide, ethylselenide and propylselenide; acylselenides such as acetylselenide and propionylselenide; phosphoroselenoamidites and phosphoroselenoate groups.

The selenium group or groups present in the selenium derivatives of the present invention may be at any position on the sugar ring of a nucleoside or nucleotide. For instance, the selenium substituent can be at the 1', 2', 3', 4', or 5' position of the ribose sugar or the 1', 3', 4', or 5' position of the deoxyribose sugar. Alternatively, the selenium may be substituted for the oxygen of the ribose or deoxyribose sugar ring.

In another embodiment the selenium substituent of the selenium derivatives of the present invention can be on a nucleic acid base. In this embodiment, the selenium derivatives of the present invention may be at any position of the nucleic acid base. Preferably, the selenium substituent is 8-selenoadenine, 8-selenoadenine triphosphate, or 8-selenoadenine phosphoramidite; 2-selenothymine, 2-selenothymine triphosphate, or 2-selenothymine phosphoramidite; 4-selenothymine, 4-selenothymine triphosphate, or 4-selenothymine phosphoramidite; 2-selenocytosine, 2-selenocytosine triphosphate, or 2-selenocytosine phosphoramidite; 6-selenoguanine, 6-selenoguanine triphosphate, or 6-selenoguanine phosphoramidite. As used herein a nucleic acid base is any naturally occurring or synthetic base found in nucleic acids, such as for instance, adenine, thymine, uracil, guanine or cytosine. In oligonucleotides or nucleic acids, the nucleic acid bases are linked to the 1' position of the ribose or deoxyribose ring of a 3'-5' sugar phosphate diester chain. These oligonucleotide or nucleic acid chains are referred to as 3'-5' oligonucleotides or 3'-5' nucleic acids.

Nucleic acid bases include adenine (A), thymine (T), uracil (U), guanine (G) and cytosine (C), as well as other naturally occurring nucleic acid base derivatives, such as for example, inosine (hypoxanthine, 6-hydroxypurine) and xanthine (2,6-dioxopurine).

A protected nucleic acid base, as used herein is a derivative of any naturally occurring or synthetic base found in nucleic acids having a protecting group at one or more positions of the base. The protecting groups useful in practicing the present invention may be any protecting group. Protecting groups are the well known in the art and include for instance, such groups as acyl groups, trityl groups, benzoyl groups, orthoester groups and isobutyl groups or any of the many protecting groups exemplified in the present specification. As used herein, orthoester groups refers to any of the well known orthoester groups, such as for instance, the bis(2-acetoxyethoxy)methyl orthoester group.

Preferred protecting groups also include the following groups for protection of the hydroxyl group at the 2'-OH position of nucleosides and nucleotides:

a). the triisopropylsilyloxymethyl (TIPSOM) group:

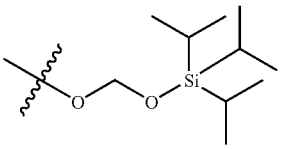

and b). the bis(2-acetoxyethoxy)methyl orthoester group:

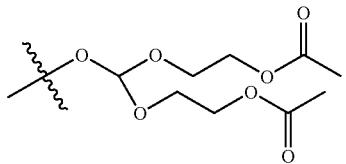

Preferred protecting groups for the protection of the amino-groups of a nucleic acid base include:

a). the phenoxyacetyl (Pac) group:

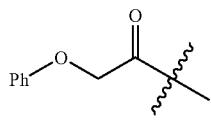

b). the isopropyl-phenoxyacetyl (iPr-Pac) group:

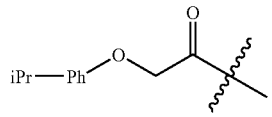

c). the dmf (N,N-dimethylformamide) group:

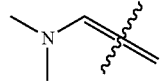

and d). the dibf (N,N-diisobutylformamide) group:

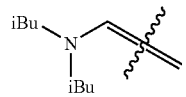

For further examples, see any review of nucleotide chemistry, such as for instance, Verma, S.; Eckstein, F., "Modified Oligonucleotides: Synthesis and Strategy for Users", *Annu. Rev. Biochem.* 1998, 67, 99-134.

The selenium derivatives of the present invention also include compounds that comprise a phosphoramidite, a phosphoroselenoamidite, a phosphate, a phosphoroselenoate, a 5'-linked nucleotide, a 5'-linked seleno-nucleotide a 5'-linked oligonucleotide, 5'-linked seleno-oligonucleotide, a 5'-linked nucleic acid chain or a 5'-linked seleno-nucleic acid chain, a 3'-linked nucleotide, a 3'-linked seleno-nucleotide a 3'-linked oligonucleotide, 3'-linked seleno-oligonucleotide, a 3'-linked nucleic acid chain or a 3'-linked seleno-nucleic acid chain.

Alternatively, the selenium derivatives of the present invention may include compounds that comprise a 3'-linked nucleotide, a 3'-linked seleno-nucleotide a 3'-linked oligonucleotide, 3'-linked seleno-oligonucleotide, a 3'-linked nucleic acid chain or a 3'-linked seleno-nucleic acid chain.

As used herein, a 5' linked nucleotide, oligonucleotide or nucleic acid chain refers to a nucleotide, oligonucleotide or nucleic acid linked through the 5' position of the ribose or deoxyribose ring. Similarly, a 3' linked nucleotide, oligonucleotide or nucleic acid chain refers to a nucleotide, oligonucleotide or nucleic acid linked through the 3' position of the ribose or deoxyribose ring.

The selenium derivatives of the present invention may be designed to have one or more protecting groups (also interchangeably referred to as blocking groups) at one or more chemically reactive positions to block reactivity with the reactive group at this position or these positions. The protecting groups are stable under the conditions of the desired reaction of the unprotected groups and may be removed by standard procedures, such as for instance, treatment with an acid or a base. By these means reactivity of groups that are not protected are available for reaction and the protected groups do not react. Many useful protecting groups are well known in the art. Some examples of protecting groups useful in the compounds and methods of the present invention include, but are not limited to orthoester, alkyl-O (such as methoxy, ethoxy, isopropyl, isobutyl etc.), acyl (may be any acyl group with from one to about 24 carbon atoms, including especially, acetyl), Bz (benzoyl), iPr (isoproponyl), iBu (isobutyryl), Ms (methylsulfonyl), TBDMS-O (tert-butyldimethylsilyloxyl), DMTr-O (dimethyltrityloxyl), and many others well known in the art. See any general organic chemistry treatise, or a text on organic chemistry, such as "Organic Chemistry of Biological Compounds" pp 281-339, R. Barker, Prentice Hall, 1971. Also, for synthetic organic and enzymatic reactions applied to nucleic acids and nucleic acid precursors, see Verma, S, and Eckstein, F. "Modified Oligonucleotides: Synthesis and Strategy for Users", Annu. Rev. Biochem. 1998, 67, 99-134.

The selenium derivatives of the present invention may be activated at any position by an activating group. The activating group is a reactive moiety that readily reacts with a compound or reagent. The activating group may be any activating group, such as for instance a phosphoramidite or a phosphoroselenoamidite group.

The selenium substituent of the selenium derivatives of the present invention may be introduced by substitution of a leaving group with an activated selenium moiety. Leaving groups are electron withdrawing groups that are readily displaced by a nucleophile. The leaving groups that may be usefully employed in the present invention include any leaving group, such as for instance, Br- (bromo-), Ts- (Tosy, p-toluenesulfonates), Bs- (Brosyl, p-bromobenzylsulfonates), Ms- (Mesyl, methylsulfonates) or Tf- (Trifyl, trifluoro methylsulfonates): See any general organic chemistry treatise, such as Morrison & Boyd, Organic Chemistry, Fourth Edition, Allyn and Bacon, publishers, Boston, 1983. The Present Invention Provides the Following Embodiments of Selenium-Containing Nucleoside, a Nucleotide, a Nucleotide Phosphoramidite, an Oligonucleotide or a Nucleic Acid Analogs:

A selenium-containing analog of a nucleoside, a nucleotide, a nucleotide phosphoramidite, an oligonucleotide or a nucleic acid having the structure of formula I:

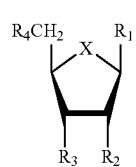

(Formula I)

wherein
(a) $R_1$ is a nucleic acid base selected from adenine, 8-selenoadenine, thymine. 2-selenothymine, 4-selenothymine, uracil, 4-selenouracil, guanine, 6-selenoguanine, cytosine and 2-selenocytosine; or is a protected nucleic acid base selected from adenine, 8-selenoadenine, thymine, 2-selenothymine, 4-selenothymine, uracil, 4-selenouracil, guanine, 6-selenoguanine, cytosine and 2-selenocytosine;
(b) $R_2$ is H, HO, alkyl-O, orthoester, TBDMS-O, HSe, diselenide, alkyl-Se;
(c) $R_3$ is H, HO, alkyl-O, TBDMS-O, HSe, diselenide, alkyl-Se, phosphoramidite, phosphoroselenoamidite, phosphate, phosphoroselenoate, a 5' linked nucleotide, a 5' linked seleno-nucleotide, a 5' linked oligonucleotide, a 5' linked seleno-oligonucleotide, a 5' linked nucleic acid chain or a 5' linked seleno-nucleic acid chain;
(d) $R_4$ is H, HO, alkyl-O, TBDMS-O, HSe, diselenide, alkyl-Se, DMTr-O, phosphate, phosphoroselenoate, diphosphate, diphosphoroselenoate, triphosphate, triphosphoroselenoate, a 3' linked nucleotide, a 3' linked oligonucleotide, a 3' linked nucleotide, a 3' linked oligonucleotide or a nucleic acid chain; and
(e) X is an oxygen atom or a selenium atom; and
wherein at least one of $R_1$, $R_2$, $R_3$, $R_4$ or X comprises at least one selenium atom, and wherein alkyl is a saturated or unsaturated, branched or unbranched hydrocarbon group having between 1 and 24 carbon atoms.

In particular aspects the above selenium-containing analog, the alkyl-Se is methyl-Se, ethyl-Se or propyl-Se.

In another aspect, the above selenium-containing analog has the following characteristics:
(a) $R_1$ is a nucleic acid base selected from adenine, thymine, uracil, guanine, 6-seleoguanine and cytosine; or $R_1$ is a protected nucleic acid base selected from adenine, thymine, uracil, guanine, 6-seleoguanine or cytosine;
(b) $R_2$ is HSe, diselenide, alkyl-Se;
(c) $R_3$ is H, HO, alkyl-O, TBDMS-O, phosphoramidite, or phosphate;
(d) $R_4$ is H, HO, DMTr-O, TBDMS-O, phosphate, diphosphate, or triphosphate; and
(e) X is an oxygen atom.

In yet another aspect, the above selenium-containing analog has the following characteristics:
(a) $R_1$ is a nucleic acid base selected from adenine, 8-selenoadenine, thymine, 2-selenothymine, 4-selenothymine, uracil, 4-selenouracil, guanine, 6-selenoguanine, cytosine and 2-selenocytosine; or $R_1$ is a protected nucleic acid base selected from adenine, 8-selenoadenine, thymine, 2-selenothymine, 4-selenothymine, uracil, 4-selenouracil, guanine, 6-selenoguanine, cytosine and 2-selenocytosine;
(b) $R_2$ is HSe, diselenide, alkyl-Se;
(c) $R_3$ is phosphoramidite;
(d) $R_4$ is DMTr-O; and
(e) X is an oxygen atom.

In yet another aspect, the above selenium-containing analog has the following characteristics:
(a) $R_1$ is a nucleic acid base selected from adenine, 8-selenoadenine, thymine, 2-selenothymine, 4-selenothymine, uracil, 4-selenouracil, guanine, 6-selenoguanine, cytosine and 2-selenocytosine;
(b) $R_2$ is HSe, diselenide, alkyl-Se;
(c) $R_3$ is HO;
(d) $R_4$ is HO; and
(e) X is an oxygen atom.

In another aspect, the above selenium-containing analog has the following characteristics:
(a) $R_1$ is a nucleic acid base selected from adenine, 8-selenoadenine, thymine, 2-selenothymine, 4-selenothymine, uracil, 4-selenouracil, guanine, 6-selenoguanine, cytosine and 2-selenocytosine;
(b) $R_2$ is HSe, diselenide, alkyl-Se;
(c) $R_3$ is HO;
(d) $R_4$ is triphosphate; and
(e) X is an oxygen atom.

In another aspect, the above selenium-containing analog has the following characteristics:
(a) $R_1$ is a nucleic acid base selected from adenine, 8-selenoadenine, thymine, 2-selenothymine, 4-selenothymine, uracil, 4-selenouracil, guanine, 6-selenoguanine, cytosine and 2-selenocytosine, or a protected nucleic acid base selected from adenine, 8-selenoadenine, thymine, 2-selenothymine, 4-selenothymine, uracil, 4-selenouracil, guanine, 6-selenoguanine, cytosine and 2-selenocytosine;

(b) $R_2$ is H, HO, alkyl-O, orthoester, TBDMSO;
(c) $R_3$ is HSe, diselenide, alkyl-Se, phosphoramidite, phosphoroselenoamidite, or phosphoroselenoate;
(d) $R_4$ is HO, DMTr-O, TBDMS-O, phosphate, diphosphate, or triphosphate; and
(e) X is an oxygen atom.

In another aspect, the above selenium-containing analog has the following characteristics:
(a) $R_1$ is a nucleic acid base selected from adenine, 8-selenoadenine, thymine, 2-selenothymine, 4-selenothymine, uracil, 4-selenouracil, guanine, 6-selenoguanine, cytosine and 2-selenocytosine, or a protected nucleic acid base selected from adenine, 8-selenoadenine, thymine, 2-selenothymine, 4-selenothymine, uracil, 4-selenouracil, guanine, 6-selenoguanine, cytosine and 2-selenocytosine;
(b) $R_2$ is H, HO, alkyl-O, TBDMSO;
(c) $R_3$ is HSe, diselenide, alkyl-Se, phosphoramidite, phosphoroselenoamidite, or phosphoroselenoate;
(d) $R_4$ is HO, DMTr-O, TBDMS-O, phosphate, diphosphate, or triphosphate; and
(e) X is an oxygen atom.

In another aspect, the above selenium-containing analog has the following characteristics:
(a) $R_1$ is a nucleic acid base selected from adenine, 8-selenoadenine, thymine, 2-selenothymine, 4-selenothymine, uracil, 4-selenouracil, guanine, 6-selenoguanine, cytosine and 2-selenocytosine;
(b) $R_2$ is H, HO;
(c) $R_3$ is alkyl-Se;
(d) $R_4$ is DMTr-O; and
(e) X is an oxygen atom.

In another aspect, the above selenium-containing analog has the following characteristics:
(a) $R_1$ is a nucleic acid base selected from adenine, 8-selenoadenine, thymine, 2-selenothymine, 4-selenothymine, uracil, 4-selenouracil, guanine, 6-selenoguanine, cytosine and 2-selenocytosine;
(b) $R_2$ is H, HO;
(c) $R_3$ is alkyl-Se;
(d) $R_4$ is HO; and
(e) X is an oxygen atom.

In another aspect, the above selenium-containing analog has the following characteristics:
(a) $R_1$ is a nucleic acid base selected from adenine, 8-selenoadenine, thymine, 2-selenothymine, 4-selenothymine, uracil, 4-selenouracil, guanine, 6-selenoguanine, cytosine and 2-selenocytosine;
(b) $R_z$ is H, HO;
(c) $R_3$ is alkyl-Se;
(d) $R_4$ is triphosphate; and
(e) X is an oxygen atom.

In another aspect, the above selenium-containing analog has the following characteristics:
(a) $R_1$ is a nucleic acid base selected from adenine, 8-selenoadenine, thymine, 2-selenothymine, 4-selenothymine, uracil, 4-selenouracil, guanine, 6-selenoguanine, cytosine and 2-selenocytosine; or $R_1$ is a protected nucleic acid base selected from adenine, 8-selenoadenine, thymine, 2-selenothymine, 4-selenothymine, uracil, 4-selenouracil, guanine, 6-selenoguanine, cytosine and 2-selenocytosine;
(b) $R_2$ is H, HO, alkyl-O, TBDMS-O or an orthoester;
(c) $R_3$ is HO, alkyl-O, phosphoranmidite, phosphate, or TBDMSO;
(d) $R_4$ is HSe, diselenide, alkyl-Se, phosphoroselenoate, diphosphoroselenoate, or triphosphoroselenoate; and
(e) X is an oxygen atom.

In another aspect, the above selenium-containing analog has the following characteristics:
(a) $R_1$ is a nucleic acid base selected from adenine, 8-selenoadenine, thymine, 2-selenothymine, 4-selenothymine, uracil, 4-selenouracil, guanine, 6-selenoguanine, cytosine and 2-selenocytosine; or $R_1$ is a protected nucleic acid base selected from adenine, 8-selenoadenine, thymine, 2-selenothymine, 4-selenothymine, uracil, 4-selenouracil, guanine, 6-selenoguanine, cytosine and 2-selenocytosine;
(b) $R_2$ is H, HO, alkyl-O or TBDMS-O;
(c) $R_3$ is HO, alkyl-O, phosphoramidite, phosphate, or TBDMSO;
(d) $R_4$ is HSe, diselenide, alkyl-Se, phosphoroselenoate, diphosphoroselenoate, or triphosphoroselenoate; and
(e) X is an oxygen atom.

In another aspect, the above selenium-containing analog has the following characteristics:
(a) $R_1$ is thymine;
(b) $R_2$ is H;
(c) $R_3$ is TBDMSO;
(d) $R_4$ is HSe, diselenide, alkyl-Se;
(e) X is an oxygen atom.

In another aspect, the above selenium-containing analog has the following characteristics:
(a) $R_1$ is thymine;
(b) $R_2$ is H;
(c) $R_3$ is HO;
(d) $R_4$ is HSe, diselenide, alkyl-Se; and
(e) X is an oxygen atom.

In another aspect, the above selenium-containing analog has the following characteristics:
(a) $R_1$ is a protected cytosine and the protecting group comprises benzoyl;
(b) $R_2$ is H;
(c) $R_3$ is TBDMSO;
(d) $R_4$ is HSe, diselenide, alkyl-Se; and
(e) X is an oxygen atom.

In another aspect, the above selenium-containing analog has the following characteristics:
(a) $R_1$ is a protected adenine and the protecting group comprises benzoyl;
(b) $R_2$ is H;
(c) $R_3$ is TBDMSO;
(d) $R_1$ is HSe, diselenide, alkyl-Se; and
(e) X is an oxygen atom.

In another aspect, the above selenium-containing analog has the following characteristics:
(a) $R_1$ is a protected guanine or 6-selenoguanine and the protecting group comprises isobutyl;
(b) $R_2$ is H;
(c) $R_3$ is TBDMSO;
(d) $R_4$ is HSe, diselenide, alkyl-Se; and
(e) X is an oxygen atom.

In another aspect, the above selenium-containing analog has the following characteristics:
(a) $R_1$ is a protected nucleic acid base selected from adenine, thymine, uracil, guanine, 6-selenoguanine or cytosine and wherein the protected nucleic acid base comprises a protecting group selected from trityl, benzoyl or iso-butyl;
(b) $R_2$ is H, HO, TBDMS-O or alkyl-O;
(c) $R_3$ is HO, a phosphoramidite moiety, or TBDMSO;
(d) $R_4$ is HSe, diselenide, alkyl-Se; and
(e) X is an oxygen atom.

In another aspect, the above selenium-containing analog has the following characteristics:
(a) $R_1$ is a nucleic acid base selected from adenine, 8-selenoadenine, thymine, 2-selenothymine, 4-selenothymine, uracil, 4-selenouracil, guanine, 6-selenoguanine, cytosine and 2-selenocytosine; or a protected nucleic acid base selected from adenine, 8-selenoadenine, thymine, 2-selenothymine, 4-selenothymine, uracil, 4-selenouracil, guanine, 6-selenoguanine, cytosine and 2-selenocytosine, and wherein the protected nucleic acid base comprises a protecting group selected from acetyl, trityl, benzoyl or iso-butyl;
(b) $R_2$ is H, HO, TBDMS-O or alkyl-O;
(c) $R_3$ is HO, or TBDMS-O;
(d) $R_4$ is HSe, diselenide, alkyl-Se; and
(e) X is an oxygen atom.

In another aspect, the above selenium-containing analog has the following characteristics:
(a) $R_1$ is a nucleic acid base selected from adenine, 8-selenoadenine, thymine, 2-selenothymine, 4-selenothymine, uracil, 4-selenouracil, guanine, 6-selenoguanine, cytosine and 2-selenocytosine; or $R_1$ is a protected nucleic acid base selected from adenine, 8-selenoadenine, thymine, 2-selenothymine, 4-selenothymine, uracil, 4-selenouracil, guanine, 6-selenoguanine, cytosine and 2-selenocytosine, and wherein the protected nucleic acid base comprises a protecting group selected from trityl, benzoyl or iso-butyl;
(b) $R_2$ is H, HO, alkyl-O, orthoester, TBDMS-O;
(c) $R_3$ is HO, alkyl-O, TBDMS-O, phosphoramidite, or phosphate;
(d) $R_4$ is HO, DMTr-O, TBDMS-O, phosphate, diphosphate, or triphosphate; and
(e) X is a selenium atom.

In another aspect, the above selenium-containing analog has the following characteristics:
(a) $R_1$ is a nucleic acid base selected from adenine, 8-selenoadenine, thymine, 2-selenothymine, 4-selenothymine, uracil, 4-selenouracil, guanine, 6-selenoguanine, cytosine and 2-selenocytosine;
(b) $R_2$ is H, HO or TBDMS-O;
(c) $R_3$ is H, HO;
(d) $R_4$ is triphosphate; and
(e) X is a selenium atom.

In another aspect, the above selenium-containing analog has the following characteristics:
(a) $R_1$ is a protected nucleic acid base selected from adenine, 8-selenoadenine, thymine, 2-selenothymine, 4-selenothymine, uracil, 4-selenouracil, guanine, 6-selenoguanine, cytosine and 2-selenocytosine, and wherein the protected nucleic acid base comprises a protecting group selected from trityl, benzoyl or iso-butyl;
(b) $R_2$ is H, HO, alkyl-O or TBDMS-O;
(c) $R_3$ is H or HO;
(d) $R_4$ is DMTr-O; and
(e) X is a selenium atom.

In another aspect, the above selenium-containing analog has the following characteristics:
(a) $R_1$ is a protected nucleic acid base selected from adenine, 8-selenoadenine, thymine, 2-selenothymine, 4-selenothymine, uracil, 4-selenouracil, guanine, 6-selenoguanine, cytosine and 2-selenocytosine, and wherein the protected nucleic acid base comprises a protecting group selected from trityl, benzoyl or iso-butyl;
(b) $R_2$ is H, HO, alkyl-O or TBDMS-O;
(c) $R_3$ is phosphoramidite;
(d) $R_4$ is DMTr-O; and
(e) X is a selenium atom.

In another aspect, the above selenium-containing analog has the following characteristics:
(a) $R_1$ is a 6-seleno guanine or 6-selenoguanine;
(b) $R_2$ is H, HO, alkyl-O, orthoester, TBDMS-O;
(c) $R_3$ is H, HO, alkyl-O, TBDMS-O, phosphoramidite, phosphate, diphosphate, triphosphate, a 5' linked nucleotide, a 5' linked oligonucleotide, or a 5' linked nucleic acid chain;
(d) $R_4$ is H, HO, DMTr-O, TBDMS-O, phosphate, diphosphate, triphosphate, a 3' linked nucleotide, a 3' linked oligonucleotide or a nucleic acid chain; and
(e) X is an oxygen atom.

In another aspect, the above selenium-containing analog has the following characteristics:
(a) $R_1$ is a 6-selenoguanine;
(b) $R_2$ is H, HO, alkyl-O or TBDMS-O;
(c) $R_3$ is H, HO, alkyl-O, TBDMS-O, phosphoramidite, phosphate, diphosphate, triphosphate, a 5' linked nucleotide, a 5' linked oligonucleotide, or a 5' linked nucleic acid chain;
(d) $R_4$ is H, HO, DMTr-O, TBDMS-O, phosphate, diphosphate, triphosphate, a 3' linked nucleotide, a 3' linked oligonucleotide or a nucleic acid chain; and
(e) X is an oxygen atom.

In another aspect, the above selenium-containing analog has the following characteristics:
(a) $R_1$ is 6-selenoguanine;
(b) $R_2$ is H, HO;
(c) $R_3$ is H, HO;
(d) $R_4$ is triphosphate; and
(e) X is an oxygen atom.

In another aspect, the above, selenium-containing analog has the following characteristics:
(a) $R_1$ is 6-selenoguanine;
(b) $R_2$ is H, alkyl-O or TBDMS-O;
(c) $R_3$ is phosphoramidite;
(d) $R_4$ is DMTr-O; and
(c) X is an oxygen atom.

The selenium derivatives of the present invention may be synthesized according to methods herein disclosed. The process for preparing a compound of the following structure is described below:

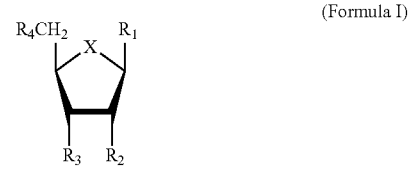

(Formula I)

in which:
(a) $R_1$ is a nucleic acid base selected from adenine, thymine, uracil and guanine, cytosine; or $R_1$ is a protected nucleic acid base selected from adenine, thymine, uracil, guanine and cytosine;
(b) $R_2$ is H, HO, alkyl-O, orthoester, TBDMSO, or $Z_i$;
(c) $R_3$ is HO, alkyl-O, phosphoramidite, phosphate or $Z_2$;
(d) $R_4$ is HO, alkyl-O, OSi(O-alkyl)$_3$, DMTr-O, phosphate, diphosphate, triphosphate or $Z_1$; and
(e) X is an oxygen atom or a selenium atom; and wherein at least one of $R_2$, $R_3$, $R_4$ comprises at least one selenium atom; and wherein $Z_1$ is HSe, diselenide, alkyl-Se; and $Z_2$ is HSe, diselenide, alkyl-Se, phosphoroselenoamidite, or phosphoroselenoate; wherein alkyl is a saturated or unsaturated, branched or unbranched hydrocarbon group having between 1 and 24 carbon atoms; and wherein at least one of $R_2$, $R_3$, or $R_4$ is either $Z_1$ or $Z_2$.

The process includes the following steps:
1). Providing a precursor, the precursor having the structure of the compound except that at least one of $Z_1$ and/or $Z_2$ is a leaving group; and
2). Reacting the precursor with a selenide ion or an alkyl selenide ion.

The reaction may be carried out in one phase (a liquid phase, preferably an aqueous phase) or in a two phase system that includes a water-immiscible organic phase and an aqueous phase and is carried out in the presence of a phase transfer catalyst. The phase transfer catalyst causes selenide ion or alkyl selenide ion transfer between the water-immiscible organic phase and the aqueous phase. The water-immiscible organic phase my be any water-immiscible organic phase, such as for example toluene, benzene or hexane.

The phase transfer catalyst may be any phase transfer catalyst that causes selenide ion or alkyl selenide ion transfer between the water-immiscible organic phase and the aqueous phase, such as for example a quaternary ammonium ion and a counterion. The counterion may be any counterion, such as for example, $F^-$, $Cl^-$, $R^-$, $I^-$, $ClO_3^-$, $NO_3^-$, $HCO_3^-$ or $HSO_4^-$.

The quaternary ammonium ions useful in the methods of the present invention are of the formula $[G_1G_2G_3G_4N]^+$, wherein the groups $G_1$, $G_2$, $G_3$, and $G_4$ may be the same or different groups. Suitable quaternary ammonium ions may comprise an aliphatic chain of between 1 and 18 carbon atoms. Quaternary ammonium ions comprising an aliphatic chain of between 1 and 12 carbon atoms are preferred. The aliphatic chain may be a saturated or an unsaturated aliphatic chain. The quaternary ammonium ions of the phase transfer catalyst may include one or more aromatic groups.

Examples of suitable quaternary ammonium ions include, but are not limited to tetramethylammonium, tetraethylammoniunm, tetrapropylammonium, tetrabutyl-ammonium, tetrapentylammonium, tetrahexylammonium, tetraheptylammoniumn: tetra-octylammonium, tetra-(n-hexyl)ammonium, tetra-[(5-methyl-hexyl)]ammonium, tetra-(5-methyl-hexenyl-2)ammonium, tetra(phenylethyl)ammonium, and N-2-phenylethyl, N-(4-methyl-hexyl), N-hexyl, N-(5-methylhexenyl-1) ammonium.

The selenium derivatives of the present invention include single stranded oligonucleotides and nucleic acid chains as well as double stranded oligonucleotides and nucleic acid chains in which some or all of the bases of one strand are paired with the bases of the second strand arranged antiparallel to the first strand.

The selenium derivatives of the present invention include oligonucleotides and nucleic acid chains useful as probes for complementary or partially complementary nucleic acids. Such hybridization probes are useful in a variety of techniques, including for instance, southern blots, northern blots and in situ techniques, such as for instance, cytohistochemical techniques for detection of specific nucleic acid sequences in situ, such as FISH (fluorescence in situ hybridization).

Alternatively, the selenium derivatives of the present invention are useful as primers for extension on complementary or partially complementary nucleic acid templates. Such priming is useful in synthetic reactions for nucleic acid sequencing, or in nucleic acid synthesis in a wide variety of applications, such as for instance, cDNA synthesis and PCR (polymerase chain reactions). For a guide to many of these techniques, see Sambrook & Russell, Molecular cloning, a Laboratory Manual. Third Ed., Cold Spring Harbor Labs., Cold Spring Harbor Press, NY, 2001.

The selenium derivatives of the present invention are especially useful in solid phase synthesis of primers having any desired sequence of nucleotides. Such primers may be synthesized in vitro by chemical or enzymatic reactions. Solid phase chemical synthesis of oligonucleotides is routine in the art and can be carried out by automated machines, such as the ABI DNA synthesizer.

The invention further provides methods for solid phase synthesis of the selenium derivatives of the present invention. The process includes providing an immobilized 3'-5' oligonucleotide or an immobilized nucleic acid chain; and providing a selenium containing activated nucleotide precursor having the structure of formula I:

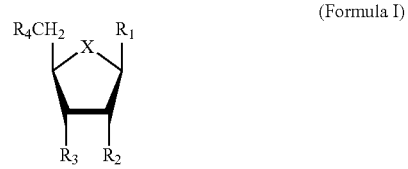

(Formula I)

in which:
(a) $R_1$ is a nucleic acid base selected from adenine, 8-selenoadenine, thymine, 2-selenothymine, 4-selenothymine, uracil, 4-selenouracil, guanine, 6-selenoguanine, cytosine and 2-selenocytosine; or $R_1$ is a protected nucleic acid base selected from adenine, 8-selenoadenine, thymine, 2-selenothymine, 4-selenothymine, uracil, 4-selenouracil, guanine, 6-selenoguanine, cytosine and 2-selenocytosine;
(b) $R_2$ is H, HO, alkyl-O, orthoester, TBDMSO, HSe, diselenide, alkyl-Se;
(c) $R_3$ is HO, alkyl-O, HSe, diselenide, alkyl-Se having an alkyl, phosphoramidite, phosphoroselenoamidite, phosphate, phosphoroselenoate, a 5' linked nucleotide, a 5' linked selenonucleotide, a 5' linked oligonucleotide, 5' linked seleno-oligonucleotide, a 5' linked nucleic acid chain or a 5' linked seleno-nucleic acid chain;
(d) $R_4$ is HO, HSe or MeSe, DMTr-O, phosphate, phosphoroselenoate, diphosphate, diphosphoroselenoate, triphosphate, or triphosphoroselenoate; and
(e) X is an oxygen atom or a selenium atom; and
wherein at least one of $R_1$, $R_2$, $R_3$, $R_4$ or X comprises at least one selenium atom, and wherein alkyl is a saturated or unsaturated, branched or unbranched hydrocarbon group having between 1 and 24 carbon atoms.

The process includes contacting the immobilized 5'-3' oligonucleotide or the immobilized 5'-3' nucleic acid chain with the selenium-containing activated nucleotide precursor under conditions suitable for addition of the activated nucleotide precursor to the immobilized 5'-3' oligonucleotide or the immobilized 5'-3' nucleic acid chain. The selenium-containing activated nucleotide precursor can be a selenium-containing 5'-activated precursor, or alternatively, the selenium-containing activated nucleotide precursor can be a selenium-containing 3'-activated precursor. The activating group of the activated nucleotide precursor may be any activating group, such as for instance a phosphoramidite group.

Moreover, the present invention further provides a process for preparing a selenium derivative of a nucleic acid, comprising:

I. providing an enzyme capable of adding a nucleotide or oligonucleotide to an oligonucleotide or a nucleic acid chain;
II. providing a nucleotide, oligonucleotide or a nucleic acid chain and a selenium-containing nucleotide or a selenium-containing oligonucleotide or a selenium-containing nucleic acid chain of the formula I:

(Formula I)

in which:
(a) $R_1$ is a nucleic acid base selected from adenine, 8-selenoadenine, thymine, 2-selenothymine, 4-selenothymine, uracil, 4-selenouracil, guanine, 6-selenoguanine, cytosine and 2-selenocytosine;
(b) $R_2$ is IT, HO, alkyl-O, orthoester, HSe, diselenide, alkyl-Se;
(c) $R_3$ is HO, alkyl-O, HSe, diselenide, alkyl-Se having an alkyl chain of between 1 and 24 carbon atoms, phosphoramidite, phosphoroselenoamidite, phosphate, phosphoroselenoate, a 5' linked nucleotide, a 5' linked seleno-nucleotide, a 5' linked oligonucleotide, 5' linked seleno-oligonucleotide, a 5' linked nucleic acid chain or a 5' linked seleno-nucleic acid chain;
(d) $R_4$ is HO, HSe or MeSe, phosphate, diphosphate, triphosphate, a 3' linked nucleotide, a 3' linked oligonucleotide or a 3' linked nucleic acid chain; and
(e) X is an oxygen atom or a selenium atom; and
wherein at least one of $R_1$, $R_2$, $R_3$, $R_4$ or X comprises at least one selenium atom and wherein alkyl is a saturated or unsaturated, branched or unbranched hydrocarbon group having between 1 and 24 carbon atoms; and wherein $R_3$ or $R_4$ comprises an activating group;
III. the process includes contacting the enzyme with the substrate and the selenium-containing nucleotide or selenium-containing oligonucleotide of formula I under conditions suitable for addition of the selenium-containing nucleotide or the selenium-containing oligonucleotide to the substrate.

The selenium derivative of the nucleotide can be a selenium derivative of a ribonucleotide, or is a selenium derivative of a deoxyribonucleotide. The enzyme can be any enzyme that adds or incorporates nucleotides, oligonucleotides or nucleic acid chains to other nucleotides, oligonucleotides or nucleic acid chains. For instance the enzyme can be a DNA polymerase, an RNA polymerase, a terminal transferase, a reverse transcriptase, a DNA ligase or an RNA ligase.

In another embodiment the selenium derivatives of the present invention are useful as food supplements. Selenium containing analogs of nucleosides, nucleotides, nucleotides, oligonucleotides or nucleic acids have been implicated as anti-cancer agents and are valuable as food supplements. The selenium-containing nucleosides and nucleotides of the present invention are useful as dietary supplement as this organic form of selenium is easily taken in and utilized by body.

The selenium derivatives of the present invention are especially valuable in X-ray crystallography, where phase determination may be a rate limiting step in molecular structure determination. Heavy metal soaking of crystals is often the bet available solution, but is only partially successful. Covalent incorporation of selenium at known positions has been applied in protein structure determination. However, to date synthesis of specific selenium derivatives of nucleotides, oligonucleotides and nucleic acids has not been achieved. The present invention provides these specific selenium derivatives.

Selenium derivatives of nucleic acids, oligonucleotides, nucleotides and nucleosides have the following advantages over previously available derivatives for X-ray crystallographic applications: First, phasing power of selenium is higher than that of bromine; hence a few selenium atoms are needed per nucleotide for derivatizing large nucleic acid molecules and using MAD phasing. Second, selenium derivatives are quite stable; nucleoside and oligonucleotide derivatives containing selenium at different positions according to methods of the present invention have been prepared. (See refs. 15, 16). Third, as selenium and oxygen are from the same Family VIA in the periodic table, it is possible to use selenium to selectively replace oxygen atoms in different chemical and geometrical environments in each nucleotide (e.g., 2'-, 3'-, 5'-ribose oxygen, ribose ring oxygen, non-bridging phosphate oxygen, or oxygen on nucleobases) in order to avoid structural perturbation.

Selenium serves as an ideal scatterer in protein X-ray crystallography, where methionine sulfur is replaced by selenium for MAD phasing. (Refs. 12, 13). Furthermore, structure determination of a catalytic RNA indirectly selenium-derivatized by co-crystallization with a selenomethionine-labeled protein has been successfully accomplished using MAD technique. (Ref. 17).

As different RNA or DNA molecules under study may require selenium incorporated at different positions of a given nucleotide building block or at different sites of a nucleic acid sequence in order to avoid structural perturbation, one building block containing the label at just one position may not meet the needs of different RNA or DNA molecules.

By methods of the present invention, selenium atoms may be directly incorporated by selectively replacing the oxygen atoms in nucleic acids. Nucleoside triphosphate and phosphoramidite derivatives containing selenium at different positions may be synthesized by the methods disclosed herein, and chemical and enzymatic standard protocols may be utilized to prepare Se-nucleic acids on a large scale.

This new approach also provides an alternative method to derivatize protein/nucleic acid complexes by labeling the nucleic acids instead of the protein counterparts, which are usually more difficult to prepare. These methods will greatly facilitate three-dimensional crystal structure determination of nucleic acids and their complexes with proteins.

The present invention provides methods for synthesis of a variety of selenium-derivatized phosphoramidites and triphosphates to allow precise placement of selenium at a desired position at a given nucleotide site, or a desired nucleotide site(s) of a nucleic acid molecule.

In one embodiment, the present invention provides synthetic routes to replace nucleotide oxygen with selenium, and to incorporate selenium at the 5-position of pyrimidines and the 8-position of purines. Routes to synthesize nucleoside phosphoramidites and triphosphates with selenium replacing the 2', 3', 5', ring, α-phosphate, and base oxygen atoms are also disclosed below.

I. Synthesis of the Se-Phosphoramidites and Se-Triphosphates

Figure 2:
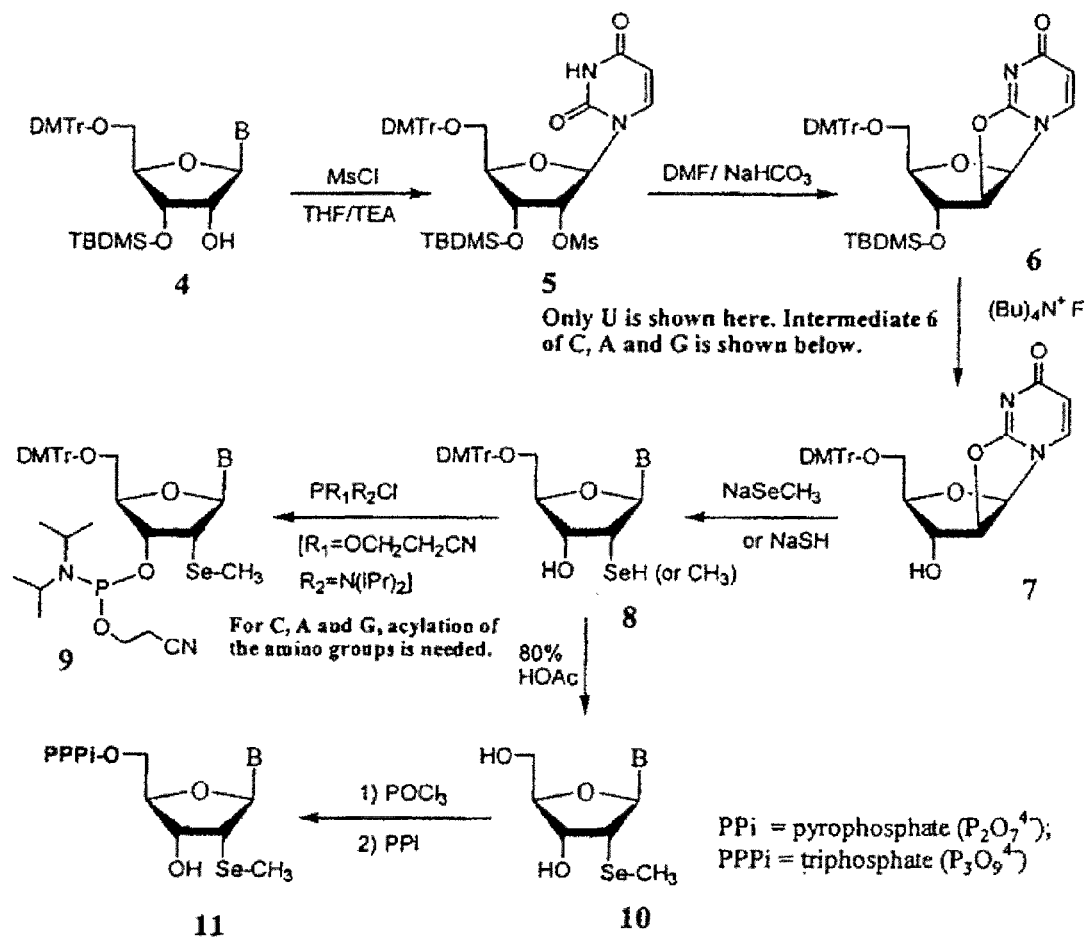
FIG. 2. Synthetic route to 2'-MeSe nucleosides, 2'-MeSe-nucleotides and 2'-MeSe-3'-phosphoramidites, showing key polycyclic intermediate of C, A and G.
Figure 2:
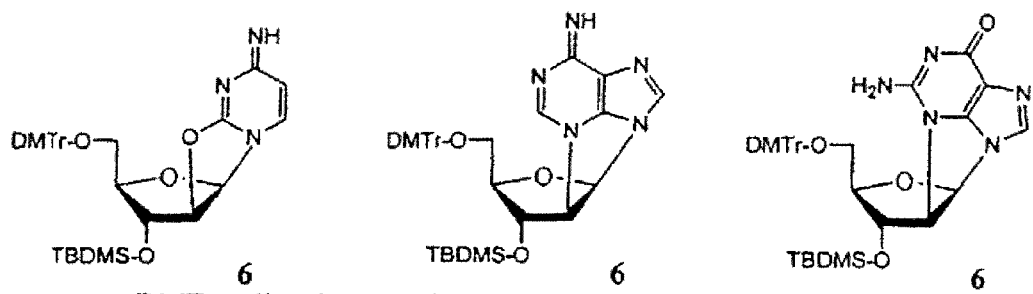

The synthetic routes for 2'-Se-nucleoside analogs are shown in FIG. 2. After mesylation of partially protected uridine 4 at 2'-position, the mesyl group (or other suitable leaving group such as tosyl) is displaced by the exo-2-oxygen of the pyrimidine, forming a fused tricyclic compound 6. (See Ref. 16): As the bulky 3'-TBDMS group blocks selenide nucleophiles attacking at 2' position, this TBDMS group is removed, for example by t-butyl ammonium fluoride treatment. 2'-Se-nucleoside 8 (FIG. 3) is formed by selenide nucleophiles attacking at the 2'-position from the α-face to open the tricyclic ring. 8 is converted to phosphoramidite 9 by reacting with 2-cyanoethyl N,N-diisopropyl-chlorophosphoramidite. C, A, and G derivatives (9 and 11) can be prepared in an analogous approach thought the base protecting groups removed during the cyclisation are needed to be reintroduced before making 9. After the deprotection of the 5'-trityl group (or other suitable group) on nucleoside derivative 8, triphosphate 11 is prepared by a triphosphorylation procedure (Ref. 15). In order to avoid hydrolysis of the triphosphates, dilute ammonia is used to remove the base protection in preparation of 2'-Se-CTP. An analogous synthetic route is useful to introduce selenium at the 3'-position.

Figure 4:
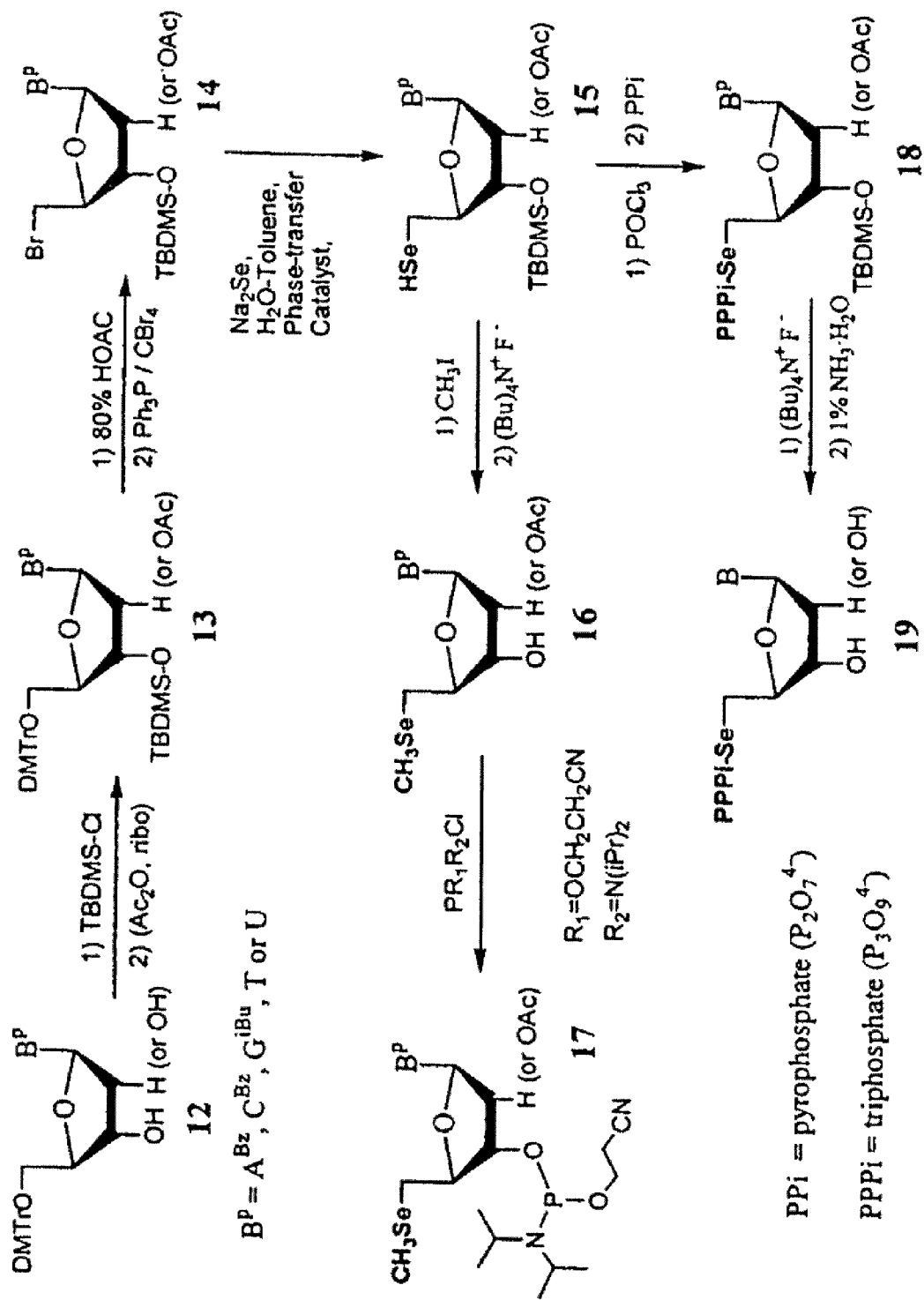
FIG. 4. Synthetic route to 5'-MeSe- and 5'-HSe-nucleosides, 5'-MeSe- and 5'-HSe-nucleotides, 5'-MeSe- and 5'-HSe-nucleotide triphosphates and 5'-MeSe- and 3'-HSe-phosphoramidites.

Synthesis of the analogs with selenium at the 5'-position is shown in FIG. 4. After removal of the 4,4'-dimethoxytrityl group (DMTr) from fully protected 13 with 80% acetic acid, bromide 14 is made by the Mitsunobu procedure. (Ref. 19). The selenium functionality is introduced via $S_N2$ displacement with sodium selenide, catalyzed by a phase-transfer catalyst. (Refs. 15, 20). Because of air oxidation, 15 forms a diselenide, which needs to be reduced before the next reaction. Phosphoramidite 17 is prepared by reacting with 2-cyanoethyl N,N-diisopropyl-chlorophosphoramidite, following the methylation protection and the silyl-deprotection of 15. The 5'-Se analogs of T and U are synthesized by this route as are the 5'-Se analogs of A, C and G. The 5'-capped phosphoramidite 17 may be used to synthesize short RNAs or DNAs labeled selenium at the 5'-termini. (Ref. 16). Nucleoside 15 is chemically phosphorylated to give 18 (Ref. 16) which is finally converted to 5'-Se-triphosphate 19 after deprotection. The selenium-phosphorus bond in 19 may be unstable and cleaved slowly in aqueous solution even at neutral pH. Thus, selenium at the external 3' and 5' positions is preferred.

Figure 5:
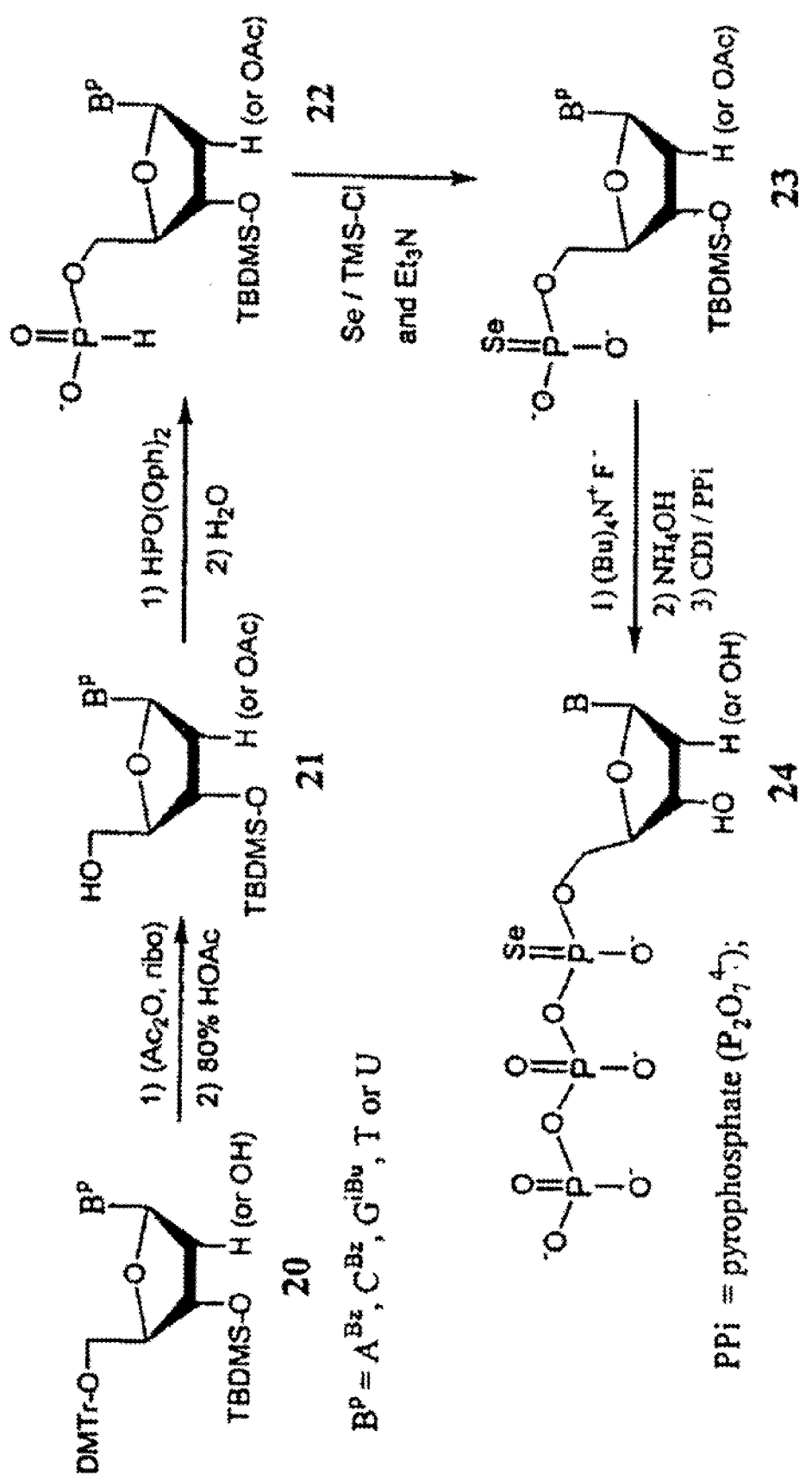
FIG. 5: Synthetic route to 5'-nucleotide triphosphoroselenoates.

The route to introduce selenium to the α-phosphate (FIG. 5), is a general route to synthesize all α-Se-NTPs and α-Se-dNTPs. Phosphoroselenonate is fairly stable though it slowly decomposes to phosphate with a half-life of approximate 30 days. (Ref. 22). As this type of decomposition is caused by air oxidation (slowly forming diselenide) followed by hydrolysis, this decomposition problem may be eliminated by conducting synthesis, storage, and crystallization under an argon atmosphere.

Tests using thymidine and uridine derivative 20 shows positive results. Partially protected thymidine and uridine 21 is prepared after 2'-acetylation (in case of uridine) and 5'-DMTr-deprotection of 20. After phosphonate 22 is prepared by treating 21 with diphenyl phosphite, selenium is incorporated to give 23 by oxidation of H-phosphonate 22 with 3H-1,2-benzothiaseleno-3-one. (Ref. 23). Following deprotection of the TBDMS group, the selenium-phosphate 23 is coupled with pyrophosphate (Ref. 24a) to give thymidine and uridine triphosphate 24 (diastereomer mixture), containing selenium on α-phosphate. (Ref. 24a). The diastereomer mixture of these nucleotides can be separated on chiral column by HPLC. Synthesis of the triphosphate analogs of A, C and G (both deoxyribonucleosides and ribonucleosides) is achieved by similar synthetic route.

Figure 6:
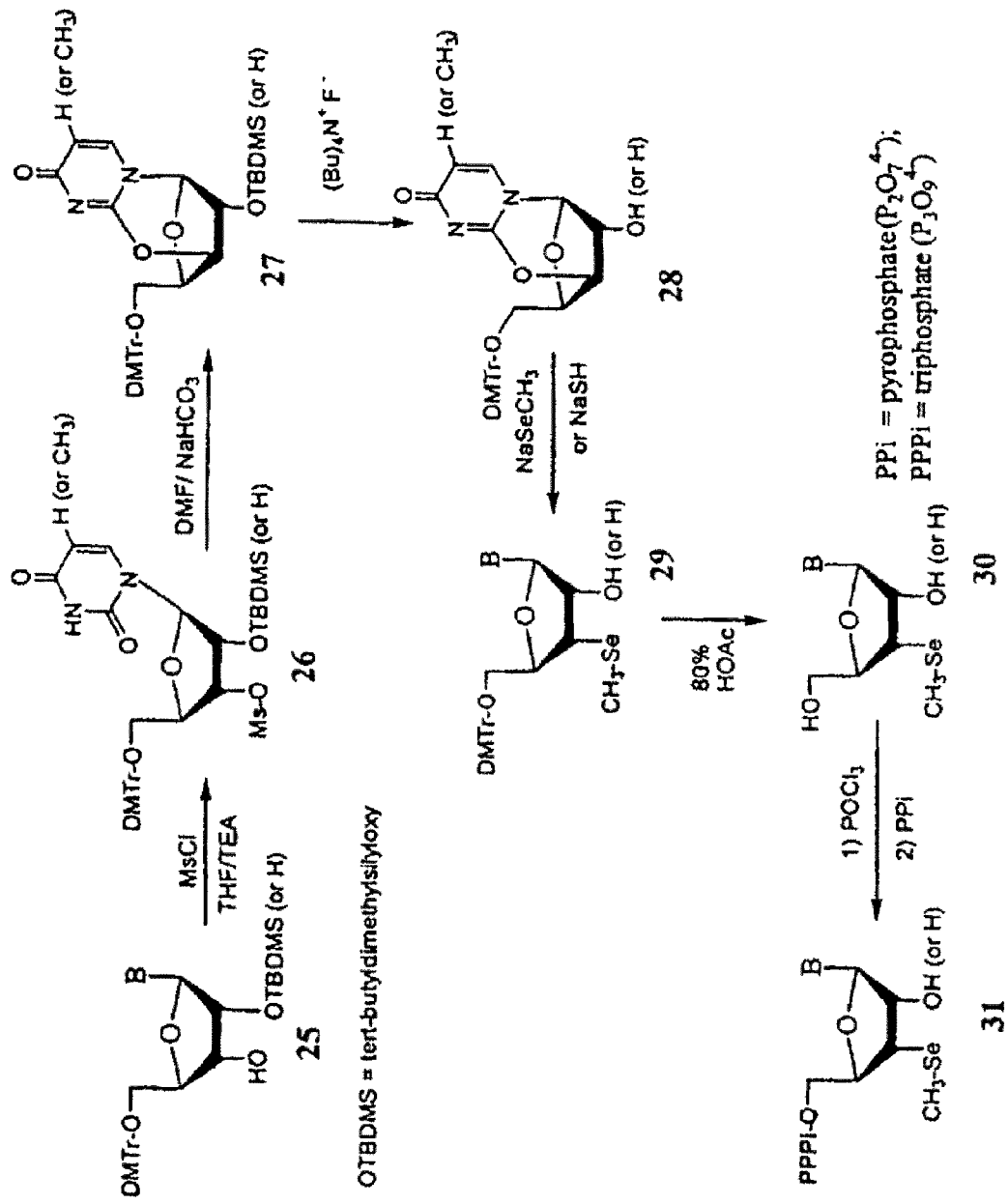
FIG. 6: Synthetic route to 3'-MeSe-5'-triphosphates.

The synthetic strategy via tricyclic intermediates 6/7 (FIG. 2) to control the stereochemistry may be applied to incorporate selenium at the 3'-position (FIG. 6). Synthesis of the uridine and thymidine derivatives is shown here, and the analogs of C, A, and G may also be prepared analogously to synthesis in FIG. 2.

Figure 7:
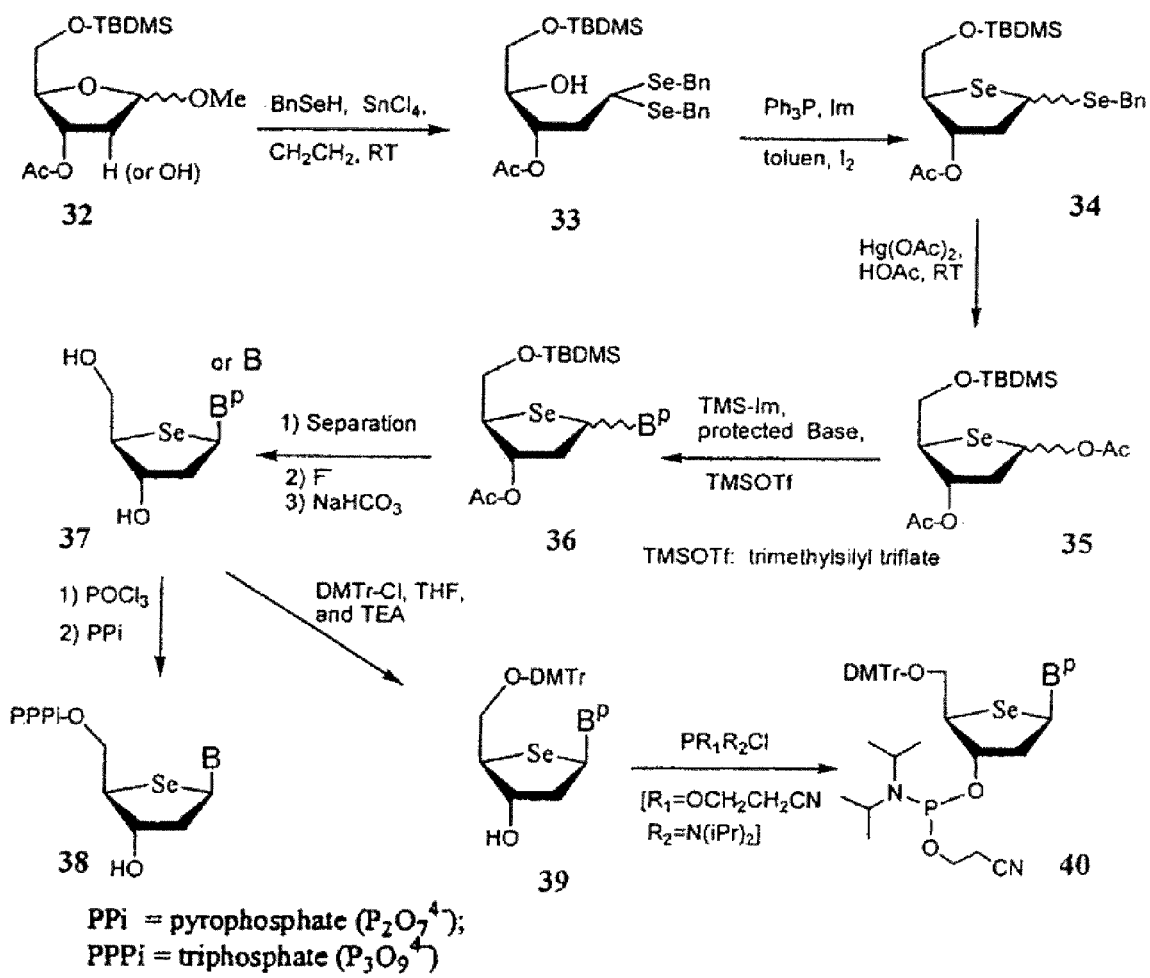
FIG. 7: Synthetic scheme for replacement of the sugar ring oxygen of a nucleoside or a nucleotide with selenium.

The synthetic strategy for replacing the sugar ring oxygen with selenium is disclosed in FIG. 7. (Ref. 24). After introducing the selenium functionality to deoxyribose (or ribose) derivative 32 via protection of the aldehyde, cyclic selenium compound 34 is made using triphenyl phosphine, which is further converted to the key intermediate 35 via displacing the benzoylselenol group. After introduction of the nucleo-bases and purification of the β-isomers, the 5', 3' and base protecting groups are removed using tetrabutylammonium fluoride and $NaHCO_3$, followed by triphosphorylation, affording the selenium-containing triphosphate 38. The compound 37 with the base protection is reprotected with a DMTr-group, followed by converting to the selenium-containing phosphoramidite 40.

Figure 8A:
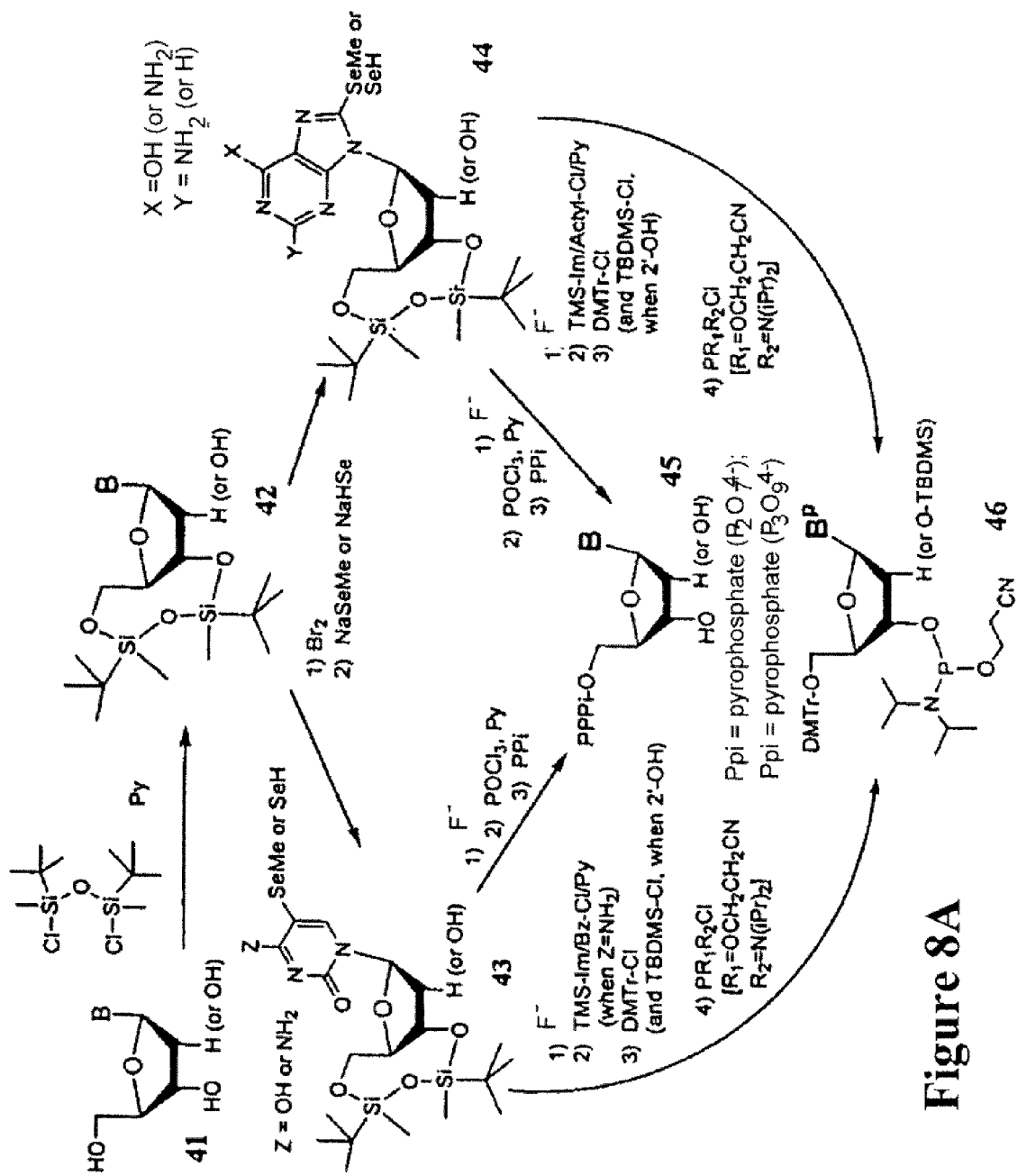
FIG. 8: Synthetic strategy for incorporating selenium into the heterocyclic base of a nucleoside or a nucleotide.
Figure 8B:
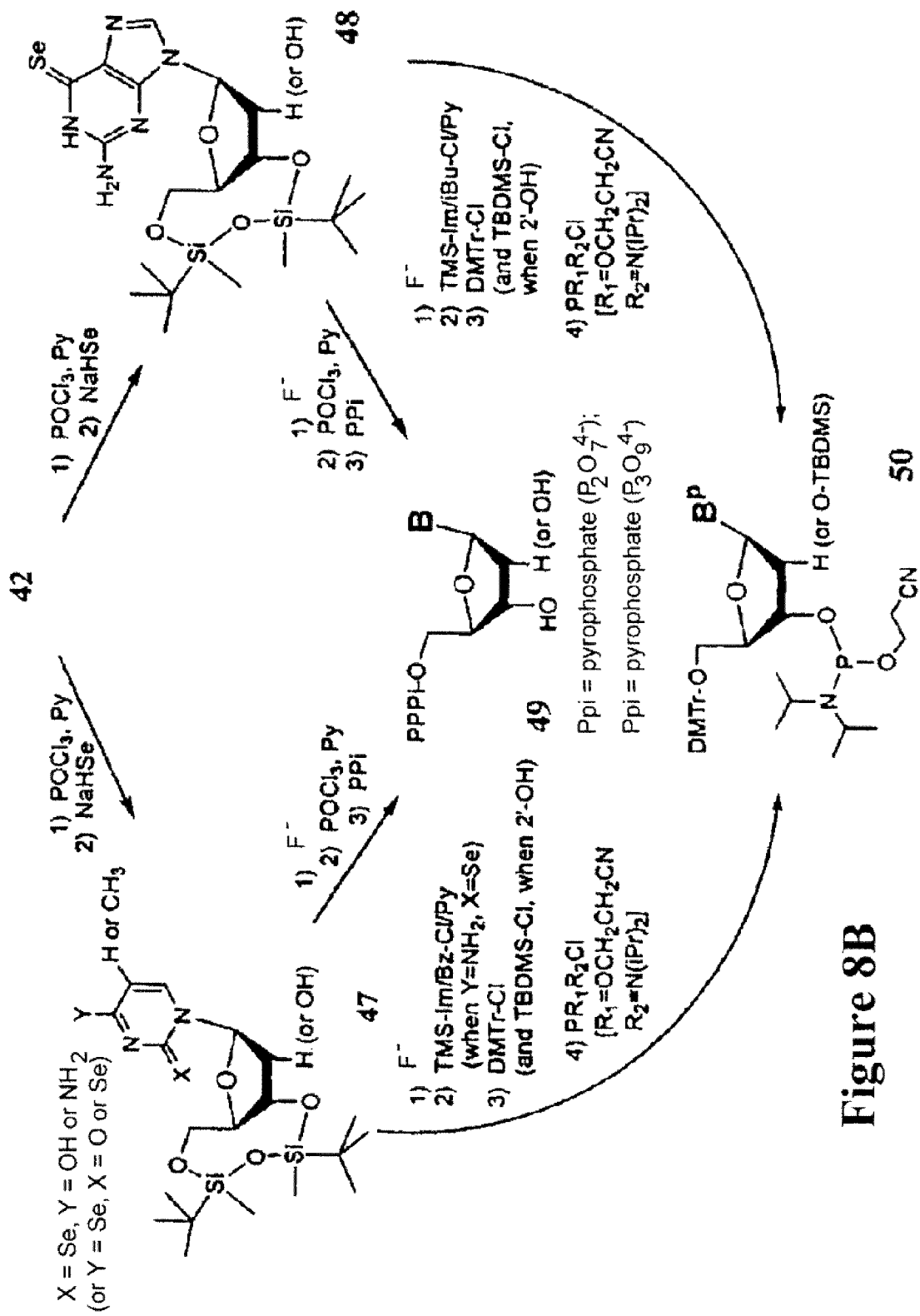

The synthetic strategy for incorporating selenium into the heterocyclic bases is disclosed in FIG. 8.

II. Preparation of RNAs and DNAs Labeled with Selenium

II.1 Chemical Synthesis of Se-RNAs

Selenium-derivatized building blocks are preferably introduced at sites away from binding and catalytic sites of functional RNA and DNA to avoid significant structure perturbation and biological property changes, and prepared Se-RNAs and Se-DNAs are preferably characterized biochemically after preparation. Results of calculating conformational perturbation from selenium substitutions at the non-bridging phosphate oxygen and 2'-position of RNA show that these sites are ideal sites for selenium replacement. It has been reported that most of the non-bridging phosphate oxygen atoms in a hairpin RNA could be replaced with sulfur, causing little or no perturbation in the RNA structure. (Ref. 25).

Mature RNAs, eg. many tRNAs and rRNAs, are methylated at 2'-hydroxyl group, (Ref. 26) and the 2'-methoxyl group facilitates C3'-endo ribose conformation, which helps to stabilize an A-Form RNA duplex. (Ref. 27). It was observed that a 2'-methylthio group also promoted the C3'-endo conformation. (Ref. 28). As sulfur and selenium are from Family VIA in the periodic table and their atomic sizes are almost the same, it is expected that the 2'-methylseleno group also promotes the C3'-endo sugar conformation, which is the favored ribose pucker; hence selenium derivatization via 2'-methylseleno-placement may have greater potential impact on X-ray crystal structure determination of RNA molecules. In these two cases, the positions of selenium incorporation are along the sugar-phosphate backbone, which should be of particular advantage in cases where proteins bound to the nucleic acid contact nucleic acid bases. As the bases are not derivatized, this will not interfere with any base interactions or any stacking interactions. As almost all DNA in complex with proteins is in the B-Form, placing selenium at the non-bridging phosphate or other sites will be favored.

Dimer (5'-$^{Se}$TT) and hexamer (5'-$^{Se}$TGCGCA) are synthesized by taking advantage of phosphoramidite chemistry. This demonstrates that the seleno-functionality is stable under the conditions of the solid-phase oligonucleotide synthesis. No oxidation of the seleno-functionality is detected, indicating the seleno-functionality is compatible with the solid-phase synthesis. Based on a calculation of X-ray phasing power of an anomalous scatterer, one selenium atom enables phase determination for RNAs up to 30 nucleotides in length. Therefore, 5'-Se-phosphoramidite 17 may be used to synthesize short 5'-Se-RNAs or 5'-Se-DNAs for MAD phasing. RNA or dsDNA oligonucleotides containing selenium atoms at both 5' and 3' termini enable phase determination up to 60 nucleotides or 60 base pairs in length. Incorporation of selenium atoms at termini provides two advantages: minimizing structural disturbance and enhancing stacking interaction in crystals because of hydrophobic nature of this selenide-functionality.

The 2'-methylseleno group promotes the C3'-endo sugar conformation, which favors A-Form duplexes. An RNA [5'-r(CGU*AC)dG-3', A-Form, Ref. 29] and an A-Form DNA (5'-GT*GTACAC-3', Ref 30) were synthesized using 2'-methylseleno-uridine phosphoramidite 9, and the 2'-methylseleno-uridine purposely incorporated into a B-Form DNA (5'-GCGTAT*ACGC-3' (SEQ ID NO: 1), Ref. 28) to investigate the potential structural perturbation which may be caused by the 2'-methylseleno group. These selenium-derivatized oligonucleotides, with selenium function at internal positions, were synthesized on solid phase and purified by HPLC. Electrospray MS of 5'-GCGTAU$_{Se}$ACGC-3' (SEQ ID NO: 2) indicated that 2'-Me-seleno-uridine is incorporated into the decamer. These oligonucleotides may be crystallized.

II.2 Preparation of Se-RNAs and Se-DNAs via Polymerization

Se-RNAs may also be prepared on DNA templates by enzymatic transcription in vitro using the Se-triphosphates as substrates, including α-Se-NTPs 24 and 2'-Se-NTPs 11. Heterogeneity (n and n+1) from transcription is not a problem for crystallization and structure determination according to the literature. (Ref. 17). Likewise, Se-DNAs may be prepared by DNA polymerization using α-Se-dNTPs 24, or prepared by polymerization using synthetic Se-DNAs as primers.

There are only four RNA (A, U, G, C) or DNA (A, T, G, C) building blocks and they are often not dramatically-biased distributed in RNAs or DNAs. Interestingly, the long fragment (25 nucleotides) of structurally characterized hammerhead ribozyme (Refs. 31, 32) contains only three uridine residues, making the ribozyme (consists of two fragments, 16 and 25 nucleotides.) an ideal RNA for Se-derivatization by this transcription approach. Besides solid-phase derivatizing synthesis, this long fragment can be derivatized by transcription using 2'-Se-UTP or α-Se-UTP together with ordinary ATP, CTP and GTP.

II.3 Se-Labeling of RNAs and DNAs via Terminal Transfer

An alternative approach to label RNAs with selenium is based on the RNA 3'-labeling method (FIG. 9). See ref. 33. After a long RNA is prepared by transcription using ordinary NTPs, α-Se-dNTPs is transferred to its 3'-terminus on a DNA template using a DNA polymerase (Klenow Fragment). Results have shown that Klenow recognized α-Se-TTP 24 as a substrate, which is consistent with DNA polymerase recognizing α-Se-dNTPs as substrates. Experiments also reveal that the number of incorporated dNTPs is dependent on the length of the overhanging nucleotides of the template, and the terminal extension reaction giving full-length product with high yields in the presence of high dNTP concentration. The products may be purified by any one of a variety of methods well known in the art, such as for example, preparative anion exchange HPLC, to single nucleotide resolution for RNA as long as 70 nucleotides. (Ref 34). This terminal transfer approach can be very useful for medium size RNAs (up to 80 nucleotides). An analogous approach can be used to prepare Se-DNAs.

II.4 Preparation of Se-RNAs and Se-DNAs Via Ligation

There is currently no satisfactory method to derivatize large nucleic acid molecules for X-ray crystallography. Methods are herein disclosed for the preparation of long Se-RNAs and Se-DNAs based on a ligation approach. (Ref. 35). Long RNAs or DNAs of interest are divided into two fragments (FIG. 10): a large fragment which is prepared by RNA transcription or DNA polymerization using ordinary triphosphates (NTPs or dNTPs), and a small fragment which is prepared by the solid-phase synthesis using Se-labeled phosphoramidites. As the transcribed large fragment contains homogeneous 5'-terminus, 3'-terminus of the synthesized small fragment is ligated to the 5'-terminus of the large one on a DNA template. Ligation experiments with ordinary oligonucleotides demonstrate that the large-scale ligation is feasible, and the ligated products are easily purified from both fragments by gel electrophoresis or HPLC.

III. Crystallization of Selenium-Derivatized Oligonucleotides and Structure Determination Crystallization conditions and X-ray crystal structures of many short RNAs [e.g., rUprA, ref. 36, r(CGUAC)dG, ref. 29, and a hammerhead ribozyme, refs. 31, 32] and short DNAs [e.g. TpT, ref. 37, TpA, ref. 38, dGpdC, ref. 39, 5'-TGCGCA, ref. 28, 5'-GCGTATACGC-3' (SEQ ID NO: 3), ref. 28, and 5'-d(GTGTACAC) ref. 30] are known. These RNAs and DNAs molecules may be derivatized with selenium according to the methods described herein, and their structures determined to verify that no structural changes have occurred and to study the structural perturbation caused by the derivatization.

As examples of this synthetic route, selenium-derivatized DNA and RNA oligonucleotides, including 5'-$^{Se}$TT, 5'-$^{Se}$TA, 5'-$^{Se}$TGCGCA (Z-DNA, Ref. 28); 5'-GCGTAU$_{Se}$ACGC-3' (SEQ ID NO: 2)) (B-Form DNA),[28] 5'-r(CGU$_{Se}$AC)dG-3' (A-Form RNA) ref. 29; and 5'-GU$_{Se}$GTACAC-3' (A-Form DNA) ref. 30; may be synthesized as described above. These oligonucleotides are suitable for crystallization. See Refs. 28-30, 37 and 38. In particular, crystal formation of the decamer (5'-GCGTAU$_{Se}$ACGC-3' (SEQ ID NO: 2)) is favored under the conditions of 2-methyl-2,4-pentanediol (10% v/v), sodium cacodylate (40 mM, pH 7.0), spermine tetrahydrochloride (12 mM), sodium chloride (80 mM), potassium chloride (12 mM), and magnesium chloride (20 mM).

Facilitation of structural determination of nucleic acids and their protein complexes will help to gather valuable information about structure-function relationship of RNAs, RNA folding, mechanism of catalytic RNAs, and nucleic acids interaction with small drug molecules and proteins. Development in this area will significantly advance RNA structural and gene regulation research. Three-dimensional structure information of catalytic RNAs, and RNA-protein and DNA-protein complexes has applications in molecular biology, genomics, biomedicine, and drug development.

The present invention also provides methods for the synthesis of oligonucleotides containing selenium at the 5'-terminus (1, FIG. 1) by incorporating the building blocks (2a and 2b), where the 5'-oxygen is substituted by selenium. As selenols are sensitive to air oxidation, 1 and 2b are protected as methyl selenides. The hydrophobic nature of the methseleno-functionality on 1 enhances strand-strand stacking interaction in crystal lattice, which in turn assists crystallization.

Incorporation of the selenium functionality is commonly accomplished by nucleophilic substitution chemistry in ethanol or DMF solvent using sodium selenide made by NaBH$_4$ reduction of selenium metal. See refs. 11a, 12a, and 13a. However, this conventional approach proved unsatisfactory in the case of acyl protected nucleosides, given the fact the strong base in the nucleophilic substitution induces removal of the acyl protecting groups on the nucleobases, along with salt formation. The present invention overcomes this problem by using a two-phase system (such as for example, H$_2$O-toluene) to incorporate selenium using a phase transfer catalyst.

To the best of Applicant's knowledge, this is the first example of selenide alkylation using a phase transfer method. The half-time of the nucleophilic reaction was less than 10 min. when Ms- (mesyl) and Br-groups were used as the leaving groups and sodium selenide was used as the nucleophile. As this nucleophilic substitution was fast in the organic phase, the selenide anions transferred into the organic phase did not cause removal of the acyl groups from the nucleosides. For C, A, and G nucleosides with acyl protection, the two-phase reactions were conducted at pH 8 (ref. 14a), which avoid the base deprotection. These reactions assisted by the phase transfer catalyst are fast, easy to workup, and give high yields (usually higher than 90% yields after purification by silica gel chromatography).

The 5'-hydroxy groups of partially protected nucleosides 3 (T, U, C, A, and G) were activated for nucleophilic substitution with the leaving groups, Br-, Ts- (tosyl), and Ms- (See scheme 1). Compound 4a was synthesized by the Mitsunobu reaction (ref. 15a), and 4b and 4c (T, C, A, and G) were synthesized by standard procedures (ref. 16a).

Scheme 1

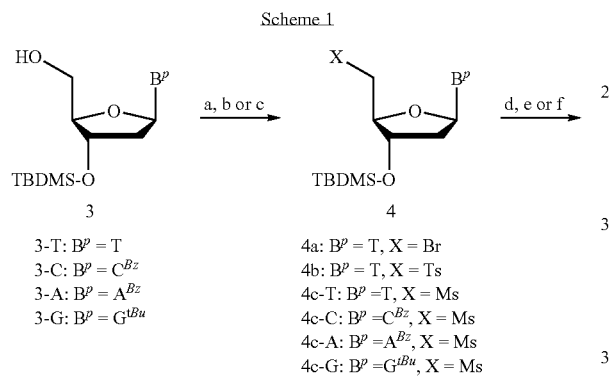

3-T: $B^p$ = T
3-C: $B^p$ = $C^{Bz}$
3-A: $B^p$ = $A^{Bz}$
3-G: $B^p$ = $G^{iBu}$

4a: $B^p$ = T, X = Br
4b: $B^p$ = T, X = Ts
4c-T: $B^p$ = T, X = Ms
4c-C: $B^p$ = $C^{Bz}$, X = Ms
4c-A: $B^p$ = $A^{Bz}$, X = Ms
4c-G: $B^p$ = $G^{iBu}$, X = Ms

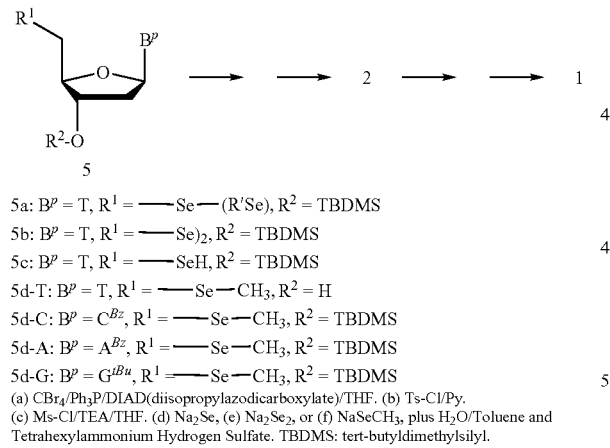

5a: $B^p$ = T, $R^1$ = —Se—(R'Se), $R^2$ = TBDMS
5b: $B^p$ = T, $R^1$ = —Se)$_2$, $R^2$ = TBDMS
5c: $B^p$ = T, $R^1$ = —SeH, $R^2$ = TBDMS
5d-T: $B^p$ = T, $R^1$ = —Se—CH$_3$, $R^2$ = H
5d-C: $B^p$ = $C^{Bz}$, $R^1$ = —Se—CH$_3$, $R^2$ = TBDMS
5d-A: $B^p$ = $A^{Bz}$, $R^1$ = —Se—CH$_3$, $R^2$ = TBDMS
5d-G: $B^p$ = $G^{iBu}$, $R^1$ = —Se—CH$_3$, $R^2$ = TBDMS (a) CBr$_4$/Ph$_3$P/DIAD(diisopropylazodicarboxylate)/THF. (b) Ts-Cl/Py. (c) Ms-Cl/TEA/THF. (d) Na$_2$Se, (e) Na$_2$Se$_2$, or (f) NaSeCH$_3$, plus H$_2$O/Toluene and Tetrahexylammonium Hydrogen Sulfate. TBDMS: tert-butyldimethylsilyl.

In order to introduce the selenium functionality, the leaving groups (Br, Ms, or Ts) with sodium selenide (Na$_2$Se), which was generated by reduction of selenium metal with NaBH$_4$ (ref. 17a) may be displaced by substitution. Because of side reactions and low solubility of the inorganic sodium selenide salt in organic solvents, such procedures for this substitution reaction in organic solvents or in aqueous solvents, or even in mixed solvents though workable, may not be optimal for all reactions. However, a two-phase system (H$_2$O-toluene) for this substitution using a phase-transfer catalyst (a quaternary ammonium ion) is efficient and optimal for bulk synthesis.

A phase-transfer catalyst (tetrahexyl-ammonium hydrogen sulfate) is used to shuttle the selenide anions from the aqueous phase to the organic phase where the reaction takes place. As the selenide ions are not solvated and are highly reactive in the organic phase, when Na$_2$Se is used as a nucleophile, the nucleophilic reaction does not stop at the selenol, which was further alkylated by another alkylating molecule, forming dialkylated product (5a). When a Ts-group (in case of 4b) is applied as the leaving group instead of Br- and Ms-groups, the substitution reaction is slowed down. Nevertheless, the formation of dialkylation product is still observed.

The disadvantage of undesired dialkylation reaction was turned into an advantage by using sodium diselenide (Na$_2$Se$_2$) instead of sodium selenide. Sodium diselenide was prepared by fully reducing selenium metal to sodium selenide with 0.3 eq. of NaBH$_1$, then adding another equivalent of selenium metal to the sodium selenide solution. The phase transfer catalyst shuttled sodium diselenide into the organic phase, where sodium diselenide was dialkylated. The dialkyl diselenide compound (5b in scheme 1) was stable, and reduction of the diselenide gave the corresponding selenol in quantitative yield. As the selenol was not stable in air, it was oxidized to the diselenide again. Therefore, the freshly prepared selenol was used for conducting the next transformation. A selenol can also be permanently protected with a stable protecting group, such as a methyl group; this protection was achieved by treatment with methyl iodide. As a permanent protection of the hydroseleno group was desired in synthesis of 1 and 2b in scheme 1, sodium methyl selenide (prepared by reduction of dimethyl diselenide with NaBH$_4$) was used as the nucleophile to react with 4c (T, C, A, and G) using the phase transfer catalyst. Although the aqueous phase was basic, this two-phase system has completely prevented the hydrolysis of the protecting acyl groups on A, C and G during the reaction, which were otherwise hydrolyzed in the basic medium.

The synthesis of oligonucleotides containing selenium at the 2'-α-position of uridine is shown below in Scheme 2.

Scheme 2

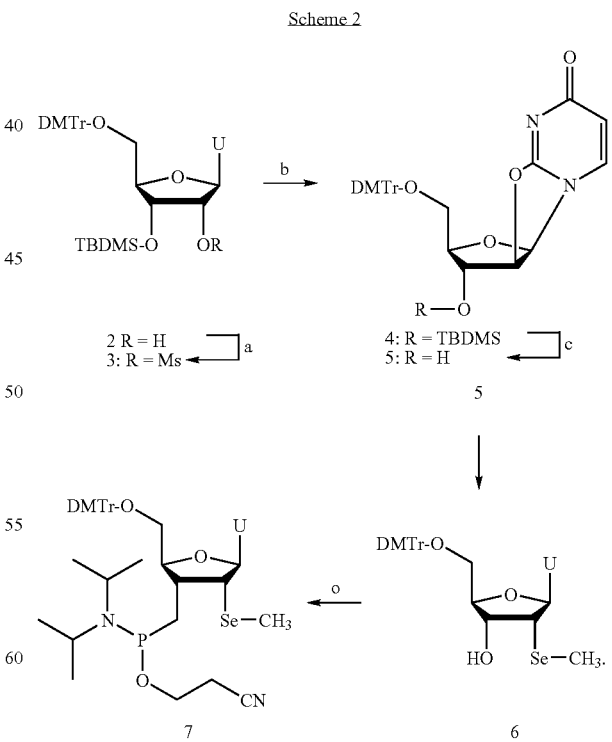

a. MsCl/THF/TEA, 95% yield; b. toluene/tetrahexylammonium hydrogen sulfate/Na$_2$CO$_3$ (sat.), 96% yield; c. (Bu)$_4$N+ F-, 95% yield; d. NaHSe, then CH$_3$I, or NaSeCH$_3$, 96%; e. PCl(OCH$_2$CH$_2$CN)N(iPr)$_2$, 92% yield.

After mesylation of partially protected uridine 2 at the 2'-position (Scheme 2), the mesyl group was displaced by the uracil exo-2-oxygen in basic conditions. A two-phase reaction system (toluene and aqueous $Na_2CO_3$), catalyzed by a phase transfer catalyst, was developed to facilitate the nucleophilic substitution; anhydio-uridine 4 was formed in 96% yield. Since our experiments indicated that the bulky 3'-TBDMS group blocked selenide nucleophiles attacking at 2' position from the α-face, this group was removed by the fluoride treatment. It was found that if NaHSe generated by reduction of selenium metal with $NaBH_4$ was used as the nucleophile to attack 5 at the 2'-position, an additional step was required to protect the resulting selenol from oxidation. When sodium methylselenide was used as the nucleophile to open the tricyclic ring of 5, selenium-nucleoside 6 was obtained in 96% yield with methyl protection, which prevents oxidation of the selenium functionality. The selenide nucleophilic reactions were conducted in THF solution, which avoided the ring opening at the 2-position, resulting in substitution at the base. Compound 6 was analyzed by MS, 77Se-NMR, 2D-NMR, and NOE experiments to confirm the stereochemistry and the structure. Nucleoside 6 was finally converted to selenium-labeled phosphoramidite 7 in 92% yield by reaction with 2-cyanoethyl N,N-diisopropyl-chlorophosphoramidite.

Using the phosphoramidite 7, DNA and RNA analogs containing selenium at the 2'-positions [DNA-octamer, 5'-GUSeGTACAC; 13 DNA-decamer, 5'-GCGTAUSeACGC-3' (SEQ ID NO: 2); 14 RNA-hexamer, and 5'-r(CGUSeAC) dG15] were synthesized following standard solid phase synthesis. The potential for scale-up was demonstrated by 10µ mole syntheses. As expected, the protected selenide functionality was found stable in mild $I_2$ treatment (20 mM, 20 seconds) for the phosphite oxidation. The Se-oligonucleotides 1 with methyl protection were purified by HPLC and the selenium functionality was confirmed by electrospray mass spectrometry.

Crystallization conditions were screened, and diffraction quality crystals were identified. X-ray fluorescence spectra confirmed the presence f selenium in crystals. MAD data of the Se-decamer to 1.2 Å resolution were collected at the Advanced Photon Source and the diffraction data were successfully phased based on the selenium anomalous signal. Likewise, diffraction data of the octamer to 1.8 Å resolution were collected, and the structure of the octamer was determined by the molecular replacement technique. These X-ray structures confirmed the presence of the 2'-methylseleno group at the α-position of the uridine.

In both structures, the 2'-Me-Se-substituted furanoses display C3'-endo puckers, consistent with the A-form geometry of the unmodified decamer and octamer duplexes, which is adopted by RNA and A-form DlNA. As previously established for 2'-O-methylated nucleotides and other 2'-O-modified ribonucleotide analogs, 14 the methyl groups of the methylseleno moieties are directed into the minor groove and the C3'-C2'-Se-Me torsion angles adopt an antiperiplanar conformation.

The Present Invention Provides the Following Synthetic Method Embodiments:

In one aspect, the invention provides a process for preparing a compound having the structure of formula I:

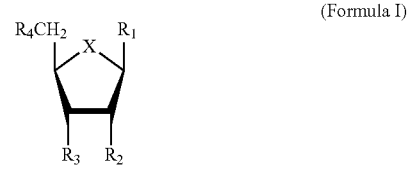

(Formula I)

wherein:
(a) $R_1$ is a nucleic acid base selected from adenine, 8-selenoadenine, thymine, 2-selenothymine, 4-selenothymine, uracil, 4-selenouracil, guanine, 6-selenoguanine, cytosine and 2-selenocytosine; or $R_1$ is a protected nucleic acid base selected from adenine, 8-selenoadenine, thymine, 2-selenothymine, 4-selenothymine, uracil, 4-selenouracil, guanine, 6-selenoguanine, cytosine and 2-selenocytosine;
(b) $R_2$ is H, HO, alkyl-O, orthoester, TBDMS-O, or Z;
(c) $R_3$ is H, HO, alkyl-O, TBDMS-O, phosphoramidite, phosphate or Z;
(d) $R_4$ is H, HO, alkyl-O, TBDMS-O, $OSi(O-alkyl)_3$, DMTr-O, phosphate, diphosphate, triphosphate or Z; and
(e) X is an oxygen atom or a selenium atom; and
wherein at least one of $R_2$, $R_3$, $R_4$ comprises at least one selenium atom; and wherein Z is HSe, diselenide, alkyl-Se, phosphoroselenoamidite, or phosphoroselenoate; wherein alkyl is a saturated or unsaturated, branched or unbranched hydrocarbon group having between 1 and 24 carbon atoms;
and wherein at least one of $R_2$, $R_3$, or $R_4$ is Z;
the process comprising:
providing a precursor, the precursor having the structure of the compound except that Z is a leaving group; and
reacting the precursor with a selenide ion or an alkyl selenide ion.

In another aspect, the invention provides a process for preparing a selenium-containing compound of formula I, wherein the process has the following characteristics: the reaction occurs in a one phase system.

In another aspect, the invention provides a process for preparing a selenium-containing compound of formula I, wherein the process has the following characteristics: the reaction occurs in a two phase system comprising a water-immiscible organic phase and an aqueous phase in the presence of a phase transfer catalyst, wherein the phase transfer catalyst causes selenide ion or alkyl selenide ion transfer between the water-immiscible organic phase and the aqueous phase.

In another aspect, the invention provides a process for preparing a selenium-containing compound of formula I, wherein the process has the following characteristics: the water immiscible organic phase comprises toluene, benzene or hexane.

In another aspect, the invention provides a process for preparing a selenium-containing compound of formula I, wherein the process has the following characteristics: the water immiscible organic phase comprises toluene.

In another aspect, the invention provides a process for preparing a selenium-containing compound of formula I, wherein the process has the following characteristics: the phase transfer catalyst comprises a quaternary ammonium ion and a counterion.

In another aspect, the invention provides a process for preparing a selenium-containing compound of formula I, wherein the process has the following characteristics: the counterion is selected from the group consisting of $F^-$, $Cl^-$, $R^-$, $I^-$, $ClO_3^-$, $NO_3^-$, $HCO_3^-$ and $HSO_4^-$.

In another aspect, the invention provides a process for preparing a selenium-containing compound of formula I, wherein the process has the following characteristics: the phase transfer catalyst is a quaternary ammonium ion of the formula $[G_1G_2G_3G_4N]^+$ and a counterion, and wherein the groups $G_1$, $G_2$, $G_3$, and $G_4$ are the same.

In another aspect, the invention provides a process for preparing a selenium-containing compound of formula I, wherein the process has the following characteristics: the phase transfer catalyst comprises an aliphatic chain of between 1 and 18 carbon atoms.

In another aspect, the invention provides a process for preparing a selenium-containing compound of formula I, wherein the process has the following characteristics: the aliphatic chain comprises a saturated aliphatic chain.

In another aspect, the invention provides a process for preparing a selenium-containing compound of formula I, wherein the process has the following characteristics: the aliphatic chain comprises an unsaturated aliphatic chain.

In another aspect, the invention provides a process for preparing a selenium-containing compound of formula 1, wherein the process has the following characteristics: the phase transfer catalyst comprises an aromatic group.

In another aspect, the invention provides a process for preparing a selenium-containing compound of formula 1, wherein the process has the following characteristics: the phase transfer catalyst comprises an ion selected from the group consisting of: tetramethylammonium, tetraethylammonium, tetrapropylammonium, tetrabutylammonium, tetrapentylammonium, tetrahexylammonium, tetraheptylammoniumn: tetraoctylammonium, tetra-(n-hexyl)ammonium, tetra-[(5-methyl-hexyl)]ammonium, tetra-(5-methyl-hexenyl-2)ammonium, tetra(phenylethyl)ammonium, and N-2-phenylethyl, N-(4-methyl-hexyl), N-hexyl, N-(5-methylhexenyl-1) ammonium.

In further aspect, the invention provides a process for preparing a selenium-containing compound of formula I, wherein the process has the following characteristics: A process for preparing a selenium derivative of a nucleic acid, comprising:

I. providing an immobilized 5'-3' oligonucleotide or an immobilized nucleic acid chain; and II. providing a selenium-containing activated nucleotide precursor having the structure of formula I:

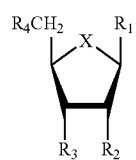

(Formula I)

wherein:

(a) $R_1$ is a nucleic acid base selected from adenine, 8-selenoadenine, thymine, 2-selenothymine, 4-selenothymine, uracil, 4-selenouracil, guanine, 6-selenoguanine, cytosine and 2-selenocytosine; or $R_1$ is a protected nucleic acid base selected from adenine, 8-selenoadenine, thymine, 2-selenothymine, 4-selenothymine, uracil, 4-selenouracil, guanine, 6-selenoguanine, cytosine and 2-selenocytosine;

(b) $R_2$ is H, HO, alkyl-O, orthoester, TBDMS-O, HSe, diselenide, alkyl-Se;

(c) $R_3$ is H, HO, alkyl-O, TBDMS-O, HSe, diselenide, alkyl-Se having an alkyl, phosphoramidite, phosphoroselenoamidite, phosphate, phosphoroselenoate, a 5' linked nucleotide, a 5' linked seleno-nucleotide, a 5' linked oligonucleotide, 5' linked seleno-oligonucleotide, a 5' linked nucleic acid chain or a 5' linked selenonucleic acid chain;

(d) $R_4$ is H, HO, HSe, diselenide, alkyl-Se, DMTr-O, TBDMS-O, phosphate, phosphoroselenoate, diphosphate, diphosphoroselenoate, triphosphate, or triphosphoroselenoate; and (e) X is an oxygen atom or a selenium atom; and wherein at least one of $R_1$, $R_2$, $R_3$, $R_4$ or X comprises at least one selenium atom, and wherein alkyl is a saturated or unsaturated, branched or unbranched hydrocarbon group having between 1 and 24 carbon atoms; and wherein $R_3$ or $R_4$ comprises an activating group;

III. contacting the immobilized 5'-3' oligonucleotide or the 5'-3' immobilized nucleic acid chain with the selenium-containing activated nucleotide precursor under conditions suitable for addition of the activated nucleotide precursor to the immobilized 5'-3' oligonucleotide or the immobilized 5'-3' nucleic acid chain.

In another aspect, the invention provides a process for preparing a selenium-containing compound of formula I, wherein the process has the following characteristics: the selenium-containing activated nucleotide precursor is a selenium-containing 5'-activated precursor.

In another aspect, the invention provides a process for preparing a selenium-containing compound of formula I, wherein the process has the following characteristics: the selenium-containing 5'-activated precursor is a selenium-containing 5'-phosphoramidite activated precursor.

In another aspect, the invention provides a process for preparing a selenium-containing compound of formula I, wherein the process has the following characteristics: the selenium-containing activated nucleotide precursor is a selenium-containing 3'-activated precursor.

In another aspect, the invention provides a process for preparing a selenium-containing compound of formula I, wherein the process has the following characteristics: the selenium-containing 3'-activated precursor is a selenium-containing 3'-phosphoramidite activated precursor.

In another aspect, the invention provides a process for preparing a selenium derivative of a nucleic acid, comprising:

I. providing an enzyme capable of adding to nucleotide or oligonucleotide into an oligonucleotide or a nucleic acid chain;

II. providing a nucleotide or oligonucleotide substrate of the enzyme and a selenium-containing nucleotide or a selenium-containing oligonucleotide or a selenium-containing nucleic acid chain of the formula I:

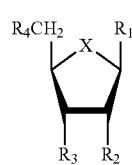

(Formula I)

wherein:
- (a) $R_1$ is a nucleic acid base selected from adenine, 8-selenoadenine, thymine, 2-selenothymine, 4-selenothymine, uracil, 4-selenouracil, guanine, 6-selenoguanine, cytosine and 2-selenocytosine;
- (b) $R_2$ is H, HO, alkyl-O, TBDMS-O, HSe, diselenide, alkyl-Se;
- (c) $R_3$ is H, HO, alkyl-O, TBDMS-O, HSe, diselenide, alkyl-Se, phosphoramidite, phosphoroselenoamidite, phosphate, phosphoroselenoate, a 5' linked nucleotide, a 5' linked seleno-nucleotide, a 5' linked oligonucleotide, 5' linked seleno-oligonucleotide, a 5' linked nucleic acid chain or a 5' linked seleno-nucleic acid chain;
- (d) $R_4$ is H, HO, alkyl-O, TBDMS-O, HSe, diselenide, alkyl-Se, phosphoramidite, phosphoroselenoamidite, phosphoroselenoate, phosphate, diphosphate, diphosphoroselenoate, triphosphate, triphosphoroselenoate, a 3' linked nucleotide, a 3' linked oligonucleotide or a nucleic acid chain; and
- (e) X is an oxygen atom or a selenium atom; and wherein at least one of $R_1$, $R_2$, $R_3$, $R_4$ or X comprises at least one selenium atom and wherein alkyl is a saturated or unsaturated, branched or unbranched hydrocarbon group having between 1 and 24 carbon atoms;

III. contacting the enzyme with substrate and the selenium-containing nucleotide or selenium-containing oligonucleotide of formula I under conditions suitable for addition of the selenium-containing nucleotide or the selenium-containing oligonucleotide to the substrate.

In another aspect, the invention provides a process for preparing a selenium-containing compound of formula I, wherein the process has the following characteristics: the selenium derivative of the nucleotide is a selenium derivative of a ribonucleotide.

In another aspect, the invention provides a process for preparing a selenium-containing compound of formula I, wherein the process has the following characteristics: the selenium derivative of the nucleotide is a selenium derivative of a deoxyribonucleotide.

In another aspect, the invention provides a process for preparing a selenium-containing compound of formula I, wherein the process has the following characteristics: the enzyme is an DNA polymerase, an RNA polymerase, a terminal transferase, a reverse transcriptase, a DNA ligase or an RNA ligase.

The Present Invention also Provides the Following Foodstuff Embodiments:

The invention provides a food supplement comprising a selenium-containing analog of a nucleoside, a nucleotide, an oligonucleotide or a nucleic acid of the structure of formula I:

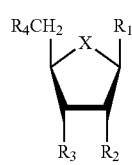

(Formula I)

- (a) $R_1$ is a nucleic acid base selected from adenine, 8-selenoadenine, thymine, 2-selenothymine, 4-selenothymine, uracil, 4-selenouracil, guanine, 6-selenoguanine, cytosine and 2-selenocytosine;
- (b) $R_2$ is H, HO, alkyl-O, TBDMS-O, orthoester, HSe, diselenide, alkyl-Se;
- (c) $R_3$ is H, HO, alkyl-O, TBDMS-O, HSe, diselenide, alkyl-Se, phosphate, phosphoroselenoate, a 5' linked nucleotide, a 5' linked seleno-nucleotide a 5' linked oligonucleotide, 5' linked seleno-oligonucleotide, a 5' linked nucleic acid chain or a 5' linked seleno-nucleic acid chain;
- (d) $R_4$ is H, HO, TBDMS-O, HSe, diselenide, alkyl-Se, phosphate, phosphoroselenoate, diphosphate, diphosphoroselenoate, triphosphate, triphosphoroselenoate, a 3' linked nucleotide, a 3' linked oligonucleotide or a nucleic acid chain; and
- (e) X is an oxygen atom or a selenium atom; and wherein at least one of $R_1$, $R_2$, $R_3$, $R_4$ or X comprises at least one selenium atom, and wherein alkyl is a saturated or unsaturated, branched or unbranched hydrocarbon group having between 1 and 24 carbon atoms.

EXAMPLES

Most solvents and reagents were purchased from Sigma, Fluka, or Aldrich (p.a.) and used without purification unless mentioned otherwise. Triethylamine (TEA) was dried over KOH (s) and distilled under argon. When necessary, solid reagents were dried under high vacuum. Reactions with compounds sensitive to air or moisture were performed under argon. Solvent mixtures are indicated as volume/volume ratios. Thin layer chromatography (TLC) was run on Merck 60 $F_{254}$ plates (0.25 mm thick; $R_f$ values in the text are for the title products), and visualized under UV-light or by a Ce—Mo staining solution (phosphomolybdate, 25 g; $Ce(SO_4)_2 \cdot 4H_2O$, 10 g; $H_2SO_4$, 60 mL, conc.; $H_2O$, 940 mL) with heating. Preparative TLC was performed using Merck 60 $F_{254}$ pre-coated plates (2 mm thick). Flash chromatography was performed using Fluka silica gel 60 (mesh size 0.040-0.063 mm) using a silica gel:crude compound weight ratio of ca. 30:1. IR spectra were recorded using a Perkin-Elmer 781 in a range of 4000-500 $cm^{-1}$. UV spectra were recorded using a Shimadzu Spectrometer (UV/VIS Model 240). $^1$H-NMR and $^{13}$C-NMR spectra were recorded using a Varian EM-600 (600 MHz) or Bruker WM-250 (250 MHz). All chemical shifts (δ) are in ppm relative to tetramethylsilane and all coupling constants (J) are in Hz. MS spectra were recorded using a Hitachi-Perkin-Elmer (RMU-6M) for EI-MS, a Kratos AEI (MS-5) for FAB-MS and ESI-MS.

Example 1

1-[(2R,4S,5R)-4-tert-butyldimethylsilyloxy-5-bromomethyl-tetrahydro-furan-2-yl]-thymidine (4a)

3-T (261.1 mg, 0.733 mmol) and $Ph_3P$ (577.5 mg, 2.2 mmol, 3 eq.) were placed in a 25-mL round-bottom flask and dried on high vacuum for 1 hr. THF (7.33 ml., final conc. 0.1 M), TEA (614 μL, 6 eq.), and CBr$_4$ (729.72 mg, 2.2 mmol, 3 eq.) were then added sequentially. The reaction mixture was stirred at RT under dry argon. The reaction was completed after 15 min as indicated by silica gel TLC (5% MeOH/ CH$_2$C$_2$, R$_f$=0.46). MeOH (0.5 mL) was then added to consume any excess reagent, and the reaction mixture was stirred for another 15 min. All the solvents were removed by rotary evaporation under reduced pressure at 30° C. The crude product was then dissolved in EtOAc, the salt was removed by filtration, and the solvent was evaporated. The residue was directly applied to a silica gel column (25 g of silica gel), and the column was eluded with EtOAc/Hexane (3:7). This solution precipitated the majority of triphenylphosphoxide, which facilitated this purification. The fractions containing the pure product were combined and evaporated under reduced pressure, and the resultant product was dried on high vacuum overnight to give a brownish foamy product (298 mg, 97% yield).

$^1$H-NMR (CDCl$_3$) δ: 0.11 [(s, 6H, (CH$_3$)$_2$Si], 0.90 (s, 9H, t-Bu), 1.94 (s, 3H, 5-CH$_3$), 2.11-2.39 (m, 2H, 3'-H), 3.58-3.72 (m, 2H, 5"-H), 4.0-4.13 (m, 1H, 5'-H), 4.35-4.48 (m, 1H, 3'-H), 6.29 (t, J=6.75 Hz, 1H, 2'-H), 7.45 (s, 1H, 6-H), 9.65-9.78 (b, 1H, NH, exchangeable by D$_2$O).

$^{13}$C-NMR (CDCl$_3$) δ: 12.60 (5-CH$_3$), 17.81 (CH$_3$—Si), 25.81 [(CH$_3$)$_3$C], 33.03 (C$_{5"}$), 40.52 (C$_{3'}$), 73.13 (C$_{5'}$), 84.60 (C$_{4'}$), 84.76 (C$_{2'}$), 111.20 (C$_5$), 135.58 (C$_6$), 150.35 (C$_2$), 163.95 (C$_4$).

IR (KBr): 3162, 3040, 2951, 2929, 2857, 1692, 1470, 1426, 1276, 1198, 1054, 993, 904, 838, 782, 671, 561 cm$^{-1}$.

UV (in acetonitrile): 263.8 nm.

Example 2

N$^6$-Benzoyl-1-[(2R,4S,5R)-4-tert-butyldimethylsilyloxy-5-methanesulfonyl-methyl-tetrahydrofuran-2-yl]-adenine (4c-A)

3-A (54.0 mg, 0.115 mmol) was placed in 10-mL flask and dried on high vacuum for 2 hours. THF (2.3 mL) and TEA (47 μL, 0.345 mmol, 3 eq) were then added, and the flask was placed on an ice-water bath and kept under dry argon. Methanesulfonyl chloride (13 μL, 0.17 mmol, 1.5 eq) was added and the reaction was completed in 15 min. (silica gel TLC in 5% MeOH/CH$_2$Cl$_2$, 4c-A R$_f$=0.35, 3-A R$_f$=0.30). MeOH (1 mL) was added to consume the excess reagent and the reaction was stirred for another 15 minutes. The solvents were removed by rotary evaporation at 40° C.; the residue was dissolved in EtOAc (15 mL), and the solution was filtered. The filtrate was then evaporated, and the residue was purified on silica gel G60 column (gradient, from 0 to 5% MeOH/ CH$_2$Cl$_2$). The collected fractions were evaporated under reduced pressure and dried on high vacuum overnight. A colorless foamy product (4c-A) was obtained (60 mg, 98% yield).

$^1$H-NMR (CDCl$_3$). δ: 0.13 [s, 6H, (CH$_3$)$_2$Si], 0.92 (s, 9H, t-Bu), 2.45-2.55 (m, 2H, 3'-H), 2.98 (s, 3H, CH$_3$SO$_3$), 4.20-4.26 (m, 1H, 5'-H), 4.40-4.52 (m, 2H, 5"-H), 4.70-4.78 (m, 1H, 4'-H), 6.45-6.53 (t, J=6.6 Hz, 1H, 2'-H), 7.49-7.65 (m, 3H, Ar), 8.01-8.08 (m, 2H, Ar), 8.20 (s, 1H, 8-H), 8.80 (s, 1H, 2-H), 8.95-9.20 (b, 1H, NH, exchangeable with D$_2$O).

Mass spectrum. The molecular weight of 4c-A is 547. Electrospray experiment showed molecular peaks at 548 [M+H]$^+$, 570 [M+Na]$^+$.

Example 3

N$^2$-isoButyryl-1-[(2R,4S,5R)-4-tert-butyldimethylsilyloxy-5-methane-sulfonyl-methyl-tetrahydrofuran-2-yl]-guanine (4c-G)

The same procedure for 4c-A was used to prepare 4c-G. The mesylation reaction was complete in 1.5 hours. After the column chromatography over silica gel, 4c-G was obtained in 94% yield.

$^1$H-NMR (CDCl$_3$) δ: 0.15 [s, 6H, (CH$_3$)$_2$Si], 0.93 (s, 9H, t-Bu), 1.25 [s, 6H, (CH$_3$)$_2$C], 2.35-2.64 (m, 2H, 3'-H), 2.76 [sept, J=6.9 Hz, 1H, CH(CH$_3$)$_2$], 3.07 (s, 3H, CH$_3$—SO$_3$), 4.12-4.25 (m, 1H-1,5'-H), 4.31-4.52 (m, 1H, 4'-H), 4.58-4.72 (m, 2H, 5"-H), 6.21 (dd, J=6.0, 6.8 Hz, 1H, 2'-H), 7.73 (s, 1H, 8-H), 8.87-8.95 (br, 1H, NH, exchangeable by D$_2$O).

$^{13}$C-NMR (CDCl$_3$) δ: 17.84 (CH$_3$—Si), 18.82 [(CH(CH$_3$)$_2$)], 25.60 [(CH$_3$)$_3$C], 27.59 (CH$_3$SO$_3$, 36.49 [(CH(CH$_3$)$_2$)], 41.46 (C$_{3'}$), 66.35 (C$_{5"}$), 71.36 (C$_{5'}$), 86.81 (C$_{4'}$), 89.27 (C$_{2'}$), 122.48 (C$_5$), 138.47 (C$_8$), 146.89 (C$_4$) 147.36 (C$_2$), 155.86 (C$_6$).

UV (in acetonitrile): 266.8 nm.

Example 4

1[(2R,4S,5S)-4-tert-butyldimethylsilyloxy-5-diselenomethyl-tetrahydro-furan-2-yl]-thymidine (5b)

Sodium borohydride (45.1 mg, 1.2 mmol) dissolved in water (1.2 mL) was added to a 25-mL flask containing a suspension of selenium metal powder (94.3 mg, 1.19 mmol) in water (1.2 mL). The reaction was placed in an ice-bath for the first few minutes to slow down the reaction; the reaction mixture was later stirred at room temperature under argon. After the vigorous reaction had subsided (approximately 10 min), additional selenium metal powder (94.3 mg, 1.19 mmol) was added. The mixture was stirred for another 10 min and then warmed on a steam-bath for 5 min to completely dissolve all the selenium and to decompose the excess NaBH$_4$. The color of the solution was brownish red and its pH was about 10-11. This aqueous solution was injected into a 25-mL flask containing 4a (100 mg, 0.239 mmol), tetrahexylammonium hydrogen sulfate (10.7 mg, 0.0239 mmol, 0.1 eq.), and toluene (4.8 mL). The reaction was closely monitored by silica gel TLC (5% MeOH/Cl$_2$Cl$_2$, product R$_f$=0.33). After 45 min the reaction was complete. A current of air was then passed through the reaction mixture to oxidize any excess of sodium diselenide to selenium metal, which precipitated.

The crude product mixture was centrifuged to remove the precipitated selenium metal, followed by extraction twice with toluene (15 mL), and the respective organic layers were combined. This organic phase was then washed with NaHCO$_3$ (15 mL, sat.) and NaCl (15 mL, sat.). The resultant yellowish organic phase was dried over anhydrous MgSO$_4$ for 30 min, the solution was filtered, and the solvents were removed by rotary evaporation under reduced pressure at 40° C. The crude residue was then dissolved in CH$_2$Cl$_2$, and the solution was loaded onto a silica gel column (6.0 g silica gel). The column was eluted with CH$_2$Cl$_2$ (50 mL) followed by a stepwise gradient of MeOH (0-3%). The fractions containing the product were combined and the solvents were removed by rotary evaporation at 30° C. After drying on high vacuum overnight, 96 mg of the yellowish diselenide product (5b) was obtained (96% yield).

¹H-NMR (CDCl₃) δ: 0.11 [s, 6H, (CH₃)₂Si], 0.93 (s, 9H, t-Bu), 1.94 (s, 3H, 5-CH₃), 2.25-2.4 (m, 2H, 3'-H), 3.33-3.36 (m, 2H, 5''-H), 4.03-4.12 (m, 1H, 5'-H), 4.28-4.35 (m, 1H, 4'-H) 6.19 (t, J=6.6 Hz, 1H, 2'-H) 7.25 (s, 1H, 6H). 8.80-8.92 (b, 1H, NH, exchangeable by D₂O).

¹³C-NMR (CDCl₃) δ: 12.66 (CH₃—Si), 17.92 [(CH₃)₃C], 25.71 (5-CH₃), 40.41 (C₃·), 52.79 (C₅''), 74.14 (C₅·), 85.38 (C₄·), 86.04 (C₂·), 111.18 (C₅), 135.72 (C₆), 150.16 (C₂), 164.10 (C₄).

IR (KBr): 3428, 3179, 3057, 2962, 2934, 2862, 2363, 1703, 1476, 1370, 1281, 1204, 1104, 838, 782, 666 cm⁻¹.

UV (in acetonitrile): 264.4 nm.

Example 5

N⁶-Benzoyl-1-(2R,4S,5R)-4-tert-butyldimethylsilyloxy-5-methselenomethyl-tetrahydrofuran-2-yl-adenine (5d-A)

NaBH₄ (20.0 mg, 0.525 mmol) was placed in 10 mL-round flask under nitrogen. Water (1.5 mL) and dimethyl diselenide (17.0 μL, 0.175 mmol) were sequentially and slowly injected into the flask. Vigorous stirring helped to dissolve dimethyl diselenide completely, forming a colorless homogeneous solution after 5-10 minutes; the pH of the solution was higher than II. Since high pH caused the hydrolysis of the protecting benzoyl group on adenine base, and pH 7.0 or lower made the following selenide substitution very slow, the pH was adjusted to 8.0 by adding dilute HCl dropwise. 4c-A (19.2 mg, 0.0350 mmol) and tetrahexylammonium hydrogen sulfate (0.5 mg) dissolved in toluene (0.7 mL) were then added to the sodium methylselenide solution (pH 8.0) described above, and the two-phase mixture (toluene and water) was stirred under nitrogen. The reaction was complete after 5 hours, forming 5d-A (silica gel TLC, 5% MeOH/CH₂Cl₂, R_f=0.52). Longer reaction time caused slow hydrolysis of the benzoyl group (the hydrolyzed product R_f=0.33 on TLC, 5% MeOH/CH₂Cl₂). The organic phase was removed and the aqueous phase was extracted twice with EtOAc; the combined organic phase was washed twice with saturated NaCl solution. The solvents were removed by rotary evaporation under reduced pressure at 40° C. The crude product was dissolved in Cl₂Cl₂ and loaded on a silica gel TLC plate (5% MeOH/CH₂Cl₂). Colorless product was recovered from this purification (18.2 mg, 95% yield).

¹H-NMR (CDCl₃). δ: 0.12[s, 6H, (CH₃)₂Si], 0.92 (s, 9H, t-Bu), 2.02 (s, 3H, CH₃Se), 2.43-2.53 (m, 1H, 3'-H), 2.78-3.00 (m, 3H, 3'-H and 5''-H), 4.15-4.23 (m, 1H, 5'-H), 4.55-4.63 (m, 1H, 4'-H), 6.42-6.50 (t, J=6.6 Hz, 1H, 2'-H), 7.48-7.57 (m, 2H, Ar). 7.57-7.65 (m, 1H, Ar), 8.00-8.07 (m, 2H, Ar), 8.27 (s, 1H, 8-H), 8.80 (s, 1H, 2-H), 8.94-9.00 (b, 1H, NH, exchangeable by D₂O).

The molecular weight of 5d-A (C₂₄H₃₃N₅O₂SiSe) is 547 with adjustment for ⁸⁰Se isotope [average atomic weight of Se is 79, including 76 (9%), 77 (7%), 78 (23%), 80 (49%), 82 (9.2%)]. The peaks are: 546 [M(⁷⁸Se)+H]⁺, 548 [M(⁸⁰Se)+H]⁺, 550 [M(⁸²Se)+H]⁺, 568 [M(⁷⁸Se)+Na]⁺, 570 [M(⁸⁰Se)+Na]⁺, 572 [M(⁸²Se)+Na]⁺.

Example 6

1-[(2R,4S,5R)-4-tert-butyldimethylsilyloxy-5-methselenomethyl-tetrahydro-furan-2-yl]-thymidine (5d-T)

Method 1. NaBH₄ (63 mg, 1.65 mmol) was dissolved in 1.5 ml water and sealed in a 10-mL flask under nitrogen. Dimethyl diselenide (54 μL, 0.55 mmol) was slowly injected into the flask. Addition of 0.2 mL of ethanol with vigorous stirring helped to dissolve dimethyl diselenide completely; a colorless homogeneous solution was formed in 5 minutes. The solution of 4c-T (47.7 mg, 0.110 mmol) and tetrahexylammonium hydrogen sulfate (1 mg) in toluene (1.1 mL) was then added to the sodium methyl selenide solution described above. The two-phase mixture (toluene and water) was stirred under nitrogen. The reaction was complete in 3 hr. as indicated silica gel TLC (5% MeOH/CH₂Cl₂, R_f=0.40). The organic phase was removed, the aqueous phase was extracted twice with EtOAc (10 mL each time), and the combined organic phase was washed twice with saturated NaCl solution (10 mL each time). The solvents were removed by rotary evaporation under reduced pressure at 40° C. The crude product was purified on TLC (5% MeOH/CH₂Cl₂). The pure product (5d-T) was dried on high vacuum overnight to afford 44.2 mg (93% yield).

Method 2. The title compound was also made by reduction of the diselenide compound 5b with NaBH₄ in EtOH. After the yellow solution of the diselenide turned into colorless, indicating production of the selenol (5c) (approximately 5 min), CH₃I was added to protect 5e. This approach gave quantitative yield.

¹H-NMR (CDCl₃) δ: 0.05 [(s, 6H, (CH₃)₂Si], 0.88 (s, 9H, t-Bu), 1.94 (s, 3H, 5-CH₃), 2.08 (s, 3H, CH₃—Se), 2.05-2.18 and 2.28-2.40 (2m, 2H, 3'-H), 2.78-2.93 (m, 2H, 5''-H), 4.02-4.09 (m, 1H, 5'-H), 4.28-4.38 (m, 1H, 4'-H), 6.26 (t, J=6.5 Hz, 1H, 2'-H), 7.42 (s, 1H, 6-H), 8.95-9.06 (b, 1H, NH, exchangeable in D₂O).

¹³C-NMR (CDCl₃) δ: 5.66 (CH₃—Se), 12.55 (5-CH₃), 17.68 (CH₃—Si), 25.68 [(CH₃)₃C], 27.63 (C₅''), 40.63 (C₃·), 73.94 (C₅·), 84.57 (C₄·), 85.60 (C₂·), 111.11 (C₅), 135.59 (C₆), 150.18 (C₂), 163.69 (C₄).

Figure 3:
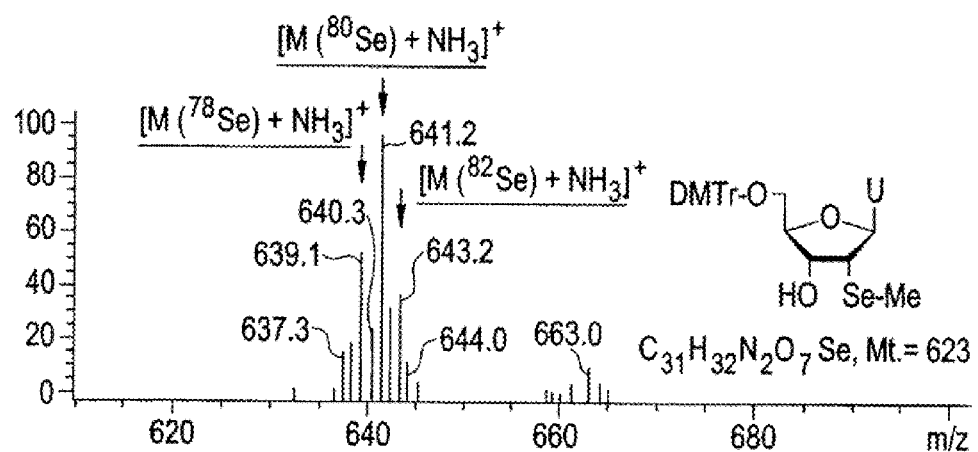
FIG. 3. Partial MS spectrum of 2'-methyl-seleno-5'-DMTr-uridine by positive electrospray in an $NH_3$—$NH_4^+$ buffer.

The 5d-T is shown in FIG. 3 (electrospray, positive ion experiment). The molecular weight (C₁₇H₃₀N₂O₄SiSe) is 434 with adjustment for ⁸⁰Se isotope. Because of binding of H or Na ions, two sets of molecular peaks are observed, in which all selenium isotopic peaks [Se 76 (9%), 77 (7%), 78 (23%), 80 (49%), 82 (9.2%)] are also observed: 431 [M (⁷⁶Se)+H]⁴, 432 [M (⁷⁷Se)+H]⁺, 433 [M (⁷⁸Se)+H]⁺, 435 [M (⁸⁰Se)+H]⁺, 437 [M (⁸²Se)+H]⁺, 453 [M (⁷⁶Se)+Na]⁺, 454 [M (⁷⁷Se)+Na]⁺, 455 [M (⁷⁸Se)+Na]⁺, 457 [M (⁸⁰Se)+Na]⁺, and 459 [M (⁸²Se)+Na]⁺.

IR (KBr): 3157, 3034, 2960, 2940, 2862, 2363, 1698, 1470, 1426, 1370, 1276, 1198, 1120, 1089, 1049, 827, 777, 682, 621 cm⁻¹.

UV (in acetonitrile): 265.2 nm.

Example 7

1-[(2R,4S,5R)-4-hydroxy-5-methselenomethyl-tetrahydrofuran-2-yl]-thymidine (5d-T-OH)

Following the standard procedure, compound 5d-T (50 mg, 0.115 mmol) was dissolved in THF (345 μL), and tert-butyl ammonium fluoride 1 M in THF (230 μL, 2 eq.) was added. The deprotection reaction was complete in 2 hours (monitored by TLC, 7.5% MeOH/CH₂Cl₂). The product was purified on TLC to give quantitative yield, and the structure of this product was confirmed by spectroscopy analysis, including ⁷⁷Se-NMR.

¹H-NMR (CD₃OD/CDCl₃=1:1) δ: 1.93 (s, 3H, 5-CH₃), 2.06 (s, 3H, CH₃—Se), 2.15-2.28 and 2.32-2.46 (2m, 2H, 3'-H), 2.82-2.96 (m, 2H, 5''-1H), 4.05-4.15 (m, 1H, 5'-H), 4.28-4.38 (m, 1H, 4'-H), 6.26 (t, J=6.7 Hz, 1H, 2'-H), 7.49 (s, 1H, 6-H), 8.95-9.06 (b, 1H, NH, exchangeable in D$_2$O).

$^{13}$C-NMR (CDCl$_3$) δ: 5.31 (CH$_3$—Se), 12.11 (5-CH$_3$), 27.49 (C$_{5''}$), 39.74 (C$_{3'}$), 72.88 (C$_{5'}$), 84.21 (C$_{4'}$), 84.14 (C2'), 110.89 (C$_5$), 135.70 (C$_6$), 150.44 (C$_2$), 163.69 (C$_4$).

As $^{77}$Se NMR active (Mr=½), a Se-NMR was done. $^{77}$Se-NMR (CDCl$_3$) δ: 362.55 ppm (reference: dibenzyl diselenide, 133.25 ppm)

IR (KBr): 3473, 3167, 3095, 2960, 2923, 2812, 2679, 1703, 1476, 1410, 1259, 1071, 1015, 950, 888, 816, 632, 570 cm$^-$.

UV (in acetonitrile): 265.0 nm.

Example 8

Synthesis of Nucleoside Analogs Containing Selenium 2'-mesyl-3'-tert-butyldimethylsilyloxy-5'-dimethoxytrityl-uridine (3)

Partially protected uridine 2 shown in scheme 2 (0.429 g, 0.65 mmol) was placed in a 25-mL round flask and dissolved in dry THF (6.5 mL, 0.1 M). Under an ice bath, triethylamine (269 µL, 1.95 mmol) and methanesulfonyl chloride (76 µL, 0.975 mmol) were then added. The reaction mixture was stirred under argon at 0° C. for 20 min [monitored on TLC, CH$_3$OH/CH$_2$Cl$_2$ (1:19), starting material R$_f$=0.37, product R$_f$=0.39]. After the reaction was complete, MeOH (0.5 mL) was added to quench the reaction; it was stirred for another 15 min. The solvents were removed under reduced pressure. The crude product was purified by flash chromatography on a silica gel column (CH$_3$OH/CH$_2$Cl$_2$; the gradients, 0.5% to 2%) to give 3 (0.455 g, 95% yield) as a white foam.

$^1$H-NMR (CD$_3$OD) δ (ppm): 0.08 and 0.21 [s, s, 2×3H, (CH$_3$)$_2$Si], 0.92 [m, 9H, (CH$_3$)$_3$CSi], 3.37 (s, 31, CH$_3$SO$_2$), 3.50-3.54 (m, 2H, H-5'), 3.88 (s, 6H, 2×CH$_3$O), 4.20-4.25 (m, 1H, H-4'), 4.63-4.67 (m, 1H, H-3'), 5.35-5.42 (m, 1H, H-2'), 5.41 (d, J=8.1 Hz, 1H, H-5), 6.19 (d, J=2.7 Hz, 1H, H-1'), 6.98-6.92 (m, 4H, Ar—H), 7.37-7.56 (m, 9H, Ar—H), 8.21 (d, J=8.2 Hz, 1H, H-6).

$^{13}$C-NMR (CD$_3$OD) δ (ppm): 19.23 (Si—CH$_3$), 26.72 [SiC(CH$_3$)$_3$], 39.57 (—SO$_3$CH$_3$), 56.28 (OCH$_3$), 62.01 (C-5'), 71.14 (C-3'), 82.52 (C-4'), 85.11 (C-2'), 89.06 (C-1'), 103.53 (C-5), 114.80, 132.04, 136.70, 145.95, 160.94 (Ar—C), 142.40 (C-6), 152.52 (C-2), 166.31 (C-4).

IR (KBr): 3450 (br.), 3068, 3030, 2950, 2839, 1702, 1610, 1519, 1460, 1380, 1256, 1188, 1110, 1054, 1010, 933, 904, 858, 782, 763, 715, 561 cm$^{-1}$.

UV (in acetonitrile), λ$_{max}$: 236.2, 268.6 nm.

FAB-HRMS: C$_{37}$H$_{47}$N$_2$O$_{10}$SiS (M+H$^+$), 739.2719 (calc. 739.2721).

Example 9

2,2'-anhydro-1-(2'-deoxy-3'-tert-butyldimethylsilyioxy-5'-O-dimethoxytrityl-β-D-ribofuranosyl)-uracil (4)

Compound 3 of scheme 2 (407 mg, 0.551 mmol) and tetrahexylammonium hydrogen sulfate (25 mg, 0.1 eq.) were dissolved in toluene (11.0 mL, 0.05M). A saturated Na$_2$CO$_3$ solution (11 mL, pH~11) was added to the previous solution. The suspension was vigorously stirred at room temperature for 3 hrs while being periodically monitored by TLC [CH$_3$OH/CH$_2$Cl$_2$ (1:19), product R$_f$=0.32]. After the reaction was complete, the suspension was extracted three times with ethyl acetate (3×15 mL). The resultant organic phases were combined, washed with NaCl (15 ml., sat.), and dried over anhydrous MgSO$_4$. After filtration, the solvent were evaporated under reduced pressure, and the crude product was purified by flash chromatography on a silica gel column (CH$_3$OH/CH$_2$Cl$_2$; the gradients, 0.5% to 3%) to afford 4 (339 mg, 96% yield) as a white foam.

$^1$H-NMR (CDCl$_3$) δ (ppm): 0.08 and 0.14 [s, s, 2×3H, (CH$_3$)$_2$Si], 0.88 [m, 9H, (CH$_3$)$_3$CSi], 2.98-3.14 (m, 2H, H-5'), 3.82 (s, 6H, 2×CH$_3$O), 4.22-4.29 (m, 1H, H-4'), 4.48-4.52 (m, 1H, H-3'), 5.03-5.09 (m, 1H, 2'), 5.98 (d, J=7.6 Hz, 1H, H-5), 6.10 (d, J=5.7 Hz, 1H, H-1'), 6.72-6.84 (m, 4H, Ar—H), 7.18-7.36 (m, 10H, H-6, 9 Ar—H).

$^{13}$C-NMR (CDCl$_3$) δ (ppm): 18.22 (Si—CH$_3$), 25.94 [SiC(CH$_3$)$_3$], 55.61 (OCH$_3$), 62.51 (C-5'), 77.17 (C-3'), 86.95 (Ar—C), 87.90 (C-4'), 89.22 (C-2'), 90.04 (C-1'), 110.87 (C-5), 113.62, 127.38, 128.22, 130.13, 134.54, 135.56, 144.50, 158.98 (Ar—C), 137.40 (C-6), 159.51 (C-2), 171.68 (C-4).

IR (KBr): 3450, 3035, 2930, 2860, 1670, 1530, 1505, 1460, 1250, 1190, 1085, 1060, 820, 790, 770, 710, 610 cm$^{-1}$.

UV (in acetonitrile), λ$_{max}$: 233.2, 281.0 nm.

FAB-HRMS: C$_{36}$H$_{43}$N$_2$O$_7$Si (M+H$^+$), 643.2838 (calc. 643.2839).

Example 10

2,2'-anhydro-1-(2'-deoxy-5'-O-dimethoxytrityl-β-D-ribofuranosyl)-uracil (5)

Compound 4 shown in scheme 2 (140.1 mg, 0.218 mmol) was placed in a 10-mL round flask and dissolved in THF (1.6 mL). A 1M solution of tertbutylammonium fluoride in THF (0.43 mL, 0.43 mmol) was then injected. The reaction mixture was stirred at room temperature for 1 hr, monitored by TLC [CH$_3$OH/CH$_2$Cl$_2$ (1.5:18.5), product R$_f$=0.15]). The solvent was evaporated under reduced pressure and the crude product was purified by flash chromatography on a silica gel column (CH$_3$OH/CH$_2$Cl$_2$; the gradients, 0.5% to 3%) to give 5 (109 mg, 95% yield) as a white, foamy product.

$^1$H-NMR (CDCl$_3$) δ (ppm): 2.99-3.18 (m, 2H, H-5'), 3:69 (s, 6H, 2×CH$_3$O), 4.29-4.36 (m, 1H, H-4'), 4.42-4.46 (m, 1H, H-3'), 5.20-5.25 (m, 1H, H-2'), 5.92 (d, J=7.5 Hz, 1H, H-5), 6.07 (d, J=5.7 Hz, 1H, H-1'), 6.98-6.79 (m, 4H, Ar—H), 7.11-7.30 (m, 10H, H-6, 9 Ar—H).

$^{13}$C-NMR (CDCl$_3$) δ (ppm): 55.20 (OCH$_3$), 62.96 (C-5'), 75.60 (C-3'), 86.16 (Ar—C), 87.64 (C-4'), 89.42 (C-2'), 90.31 (C-1'), 109.64 (C-5), 113.18, 126.91, 127.91, 129.83, 135.40, 144.39, 158.45 (Ar—C), 135.93 (C-6), 159.75 (C-2), 172.69 (C-4).

IR (KBr): 3400 (br.), 3030, 2920, 2850, 1670, 1520, 1510, 1490, 1460, 1260, 1190, 1095, 1055, 820, 770, 705, 580 cm$^{-1}$.

UV (in acetonitrile), λ$_{max}$: 233.8, 281.2 nm.

FAB-HRMS: C$_{30}$H$_{29}$N$_2$O$_7$ (M+H$^+$), 529.1976 (calc. 529.1974).

Example 11

2'-methylseleno-5'-dimethoxytrityl-uridine (Compound 6 in Scheme 2)

NaBH$_4$ (170 mg, 4.5 mmol) was placed in a 25-mL round flask, dried on high vacuum for 15 min to deplete oxygen, kept under argon, and suspended in dry THF (9 mL). Dimethyl diselenide (CH$_3$SeSeCH$_3$, 150 µL, 1.5 mmol) was slowly injected to this suspension, followed by dropwise addition of anhydrous ethanol till gas bubbles started to occur in the yellow mixture (total volume added, 0.5 mL). After the reaction mixture turned colorless (usually 5-10 min), the solution was injected to 5 (160 mg, 0.30 mmol) dissolved in THF (6 mL). The reaction was stirred under argon at room temperature and periodically monitored by TLC [$CH_3OH$/$CH_2Cl_2$ (1:19), product $R_f$=0.35]. It was complete in 3 hr. Water (3 mL) was added to the reaction, followed by the dropwise addition of 20% HOAc to the reaction until pH around 7. After evaporation of all solvents under reduced pressure at 40° C., water (5 mL) was added to the crude product, followed by EtOAc extraction (3×10 mL). The organic phases were combined and washed with NaCl (10 mL, sat.). The organic layer was dried over anhydrous $MgSO_4$, followed by filtration and solvent evaporation. The resultant residue was purified by flash chromatography on a silica gel column ($CH_3OH$/$CH_2Cl_2$; the gradients, 0.5% to 3%) to afford 6 (179 mg, 96% yield) as a white foam.

$^1$H-NMR ($CDCl_3$) δ: 2.08 (s, 3H, $CH_3Se$), 3.42-3.47 (m, 2H, H-5'), 3.49-3.54 (m, 1H, H-2'), 3.78 (s, 6H, $CH_3O$), 4.14-4.18 (m, 1H, H-4'), 4.34-4.39 (m, 1H, H-3'), 5.36 (d, J=8.0 Hz, 1H, H-5), 6.19 (d, 1H, J=3.3 Hz, H-1'), 6.86-6.92 (m, 4H, aromatic), 7.19-7.38 (m, 9H, aromatic), 7.77 (d, J=7.8 Hz, 1H, 1H, H-6), 8.48 (br, 1H, NH).

$^{13}$C-NMR ($CDCl_3$) δ: 5.18 ($SeCH_3$), 51.12 (C-2'), 55.63 ($OCH_3$), 62.8 (C-5'), 71.90 (C-3'), 84.84 (C-4'), 87.66 (Ar—C), 87.98 (C-1'), 103.05 (C-5), 113.69, 128.43, 130.42, 135.50, 144.36, 158.55, (Ar—C), 139.45 (C-6), 150.55 (C-2), 163.03 (C-4).

NOE (FIG. 2): Irradiation at 4.36 ppm (H-3') gives NOE at 2.08 ($CH_3Se$, 1.2%), 3.42-3.47 (H-5', 1.2%), 3.49-3.54 (H-2', 6.2%), 4.14-4.18 (1H-4', 2.9%), 7.19 (Ar—H, 2.5%), 7.28 (Ar—H, 1.5%), 7.77 (H-6, 1.1%); irradiation at 6.19 ppm (H-1') gives NOE at 2.08 ($CH_3Se$, 1.7%), 3.49-3.54 (H-2', 1.5%), 4.14-4.18 (H-4', 1.0%), 7.77 (H-6, 0.9%).

$^{77}$Se-NMR ($CDCl_3$) δ: −378.0 ppm (s, 1Se), reference: dibenzyl diselenide (133.25 ppm).

IR (KBr): 3450 (br.), 3080, 3030, 2940, 1705, 1610, 1520, 1460, 1390, 1245, 1190, 1090, 1045, 850, 782, 710, 590 cm$^{-1}$.

UV (in acetonitrile), $\lambda_{max}$: 236.2, 273.4 nm.

ESI-MS (positive mode): [M($^{80}$Se)+$NH_3$]$^+$ calculated 641, observed 641.2; [M($^{78}$Se)+$NH_3$]$^+$ calculated 639, observed 639.1

FAB-HRMS: $C_{31}H_{32}N_2O_7Se$ (M$^+$), 624.1376 (calc. 624.1374).

Example 12

2'-methylseleno-3'-(2-cyanoethyl-N,N-diisopropylphosphoramidite)-5'-dimethoxytrityl-uridine (Compound 7 of Scheme 2)

To a solution of 6 of scheme 2 (320 mg, 0.51 mmol) in dry $CH_2Cl_2$ (5.1 mL) under an argon atmosphere, N,N-diisopropylethylamine (0.25 mL, 1.5 mmol) and 2-cyanoethyl N,N-diisopropylchlorophosphoramidite (0.23 mL, 1.02 mmol) were added, and the mixture was stirred at room temperature for 1 hr. Reaction completion was indicated by TLC [$CH_3OH$/$Cl_2Cl_2$ (1:19), product $R_f$=0.37]. The reaction mixture was then quenched with $NaHCO_3$ (2 mL, sat.), followed by $CH_2Cl_2$ extraction (3×5 mL). The combined organic layer was washed with NaCl (10 mL, sat.) and dried over anhydrous $MgSO_4$, followed by filtration. The solvent was then evaporated under reduced pressure and the crude product was re-dissolved in $CH_2Cl_2$ (2 mL). This solution was dropwise added to petroleum ether (100 mL) under vigorous stirring; a white precipitate was formed. After pouring out the ether, the product was re-dissolved in $CH_2Cl_2$ (2 mL), and it was pre- cipitated again with petroleum ether. The precipitate was dried on high vacuum to yield a white foam (386 mg, 92%).

UV (in acetonitrile), $\lambda_{max}$: 236.6, 267.8 nm.

IR (KBr): 3450 (br.), 3070, 3030, 2930, 2850, 1715; 1610, 1505, 1480, 1390, 1250, 1180, 1090, 1045, 785, 715, 580 cm$^{-1}$.

FAB-HRMS: $C_{40}H_{50}N_4O_8PSe$ (M+H$^+$, 825.2538 (calc. 825.2532).

Example 13

Synthesis of Oligonucleotides

The syntheses of oligonucleotides were conducted on an ABI model 392 synthesizer using standard β-cyanoethylphosphoramidite solid-phase synthesis protocol with mild $I_2$ oxidation conditions (20 mM, 20 seconds). The synthesized oligonucleotides were cleaved from the beads by incubation with concentrated ammonia for 11 hr at 60° C. After filtration or centrifugation to remove the beads, ammonia was evaporated by speed vacuum. The crude residue was redissolved in water (500 uL) and the pH adjusted to 7. Reverse-phase HPLC purification of the oligonucleotides was carried out in a C4 preparative column using a 25 mM (Et)$_3$N$^+$HCO$_3^-$ buffer (pH 7) as solvent A, and 90% acetonitrile containing 10% of 25 mM (Et)$_3$N$^+$HCO$_3$ buffer (pH 7) as solvent B. The oligonucleodites were first purified with the DMTr group on. The purification was run from 0% B→20% B in 30 minutes (10 mL/min). Detrytilation was performed by incubating the oligonucleotides for 5 min in a 2% solution of trifluoroacetic acid (from a 5× stock soln), followed by quenching with an aqueous solution of thiethylamine (from a 10× stock soln) and by extracting with petroleum ether to remove the DIMTr-OH residue. Another HPLC purification was carried out to desalt the oligonucleotides.

Crystals of d-GUSeGTACAC may be formed in a single droplet: The Octamer crystallized in the conditions of 10% MPD, 40 mM sodium cacodylate (pH 6.0), 12 mM spermine tetrahydrochloride, and 80 mM potassium chloride. Crystal Size: 0.3×0.4 mm.

As the octamer and decamer DNA sequences are palindromic, they form duplexes at room temperature, with melting temperature higher than 40° C. Many crystallization conditions, including precipitant (2-methyl-2,4-pentanediol, butanol, and ethanol), sodium cacodylate buffer (pH 5.5, 6.0, 6.5, and 7.0), spermine tetrahydrochloride, cobalt hexamine, monovalent ions (sodium, lithium, and potassium), divalent ions (magnesium, barium, and strontium), were screened using hanging drop method, with the oligonucleotides (1-2 mg/mL and 2 µL per droplet),

REFERENCES

1. Nissen, P.; Hansen, J.; Ban, N.; Moore, P. B.; Steitz, T. A. The structural basis of ribosome activity in peptide bond synthesis. *Science* 2000, 289, 920-930.
1a. Lu, M.; Steitz, T. A., "Structure of *Escherichia coli* ribosomal protein L25 complexed with a 5S rRNA fragment at 1.8-A resolution", *Proc Natl Acad Sci USA* 2000, 97, 2023-2028.
2. Ban, N.; Nissen, P.; Hansen, J.; Capel, M.; Moore, P. B.; Steitz, T. A. Placement of protein and RNA structures into a 5 A-resolution map of the 50S ribosomal subunit. *Nature* 1999, 400, 841-847.
2a. Ban, N.; Nissen, P.; Hansen, J.; Capel, M.; Moore, P. B.; Steitz, T. A., "Placement of protein and RNA structures into a 5 A-resolution map of the 50S ribosomal subunit", *Nature* 1999, 400, 841-847.

3. Golden, B. L.; Gooding, A. R.; Podell, E.; Cech, T. R. A preorganized active site in the crystal structure of the Tetrahymena ribozyme. *Science* 1998, 282, 259-264.

3a. Golden, B. L.; Gooding, A. R.; Podell, E.; Cech, T. R., "A preorganized active site in the crystal structure of the Tetrahymena ribozyme", *Science* 1998, 282, 259-264.

4. Cate, J. H.; Gooding, A. R.; Podell, E.; Zhou, K.; Golden, B. L.; Szewezak, A. A.; Kundrot, C. E.; Cech, T. R.; Doudna, J. A. RNA tertiary structure mediation by adenosine platforms. *Science* 1996, 273, 1696-1699.

4a. Cate, J. H.; Gooding, A. R.; Podell, E.; Zhou, K.; Golden, B. L.; Szewezak, A. A.; Kundrot, C. E.; Cech, T. R.; Doudna, J. A., "RNA tertiary structure mediation by adenosine platforms", *Science* 1996, 273, 1696-1699.

5. a). Kim, R.; Holbrook, E. L.; Jancarik, J.; Pandit, J.; Weng X.; Bohm, A.; Kim, S.-H. High-resolution crystals and preliminary X-ray diffraction studies of a catalytic RNA. *Acta Cryst.* 1994, D50, 290-292; b). S. Holbrook, personal communication; c). M. Egli, Personal communication.

5a. Pley, H. W.; Flaherty, K. M.; Mckay, D. B., "Three-dimensional structure of a hammerhead ribozyme", *Nature* 1994, 372, 68-74.

6. a). Usman, N.; Egli, M.; Rich, A. Large scale chemical synthesis, purification and crystallization of RNA-DNA chimeras. *Nucleic Acids Res.*, 1992, 20, 6695-6699; b). Pley, H. W.; Flaherty, K. M.; Mckay, D. B., Three-dimensional structure of a hammerhead ribozyme. *Nature* 1994, 372, 68-74; c). Naber, N.; Matuska, M.; Sablin, E. P.; Pate E.; Cooke, R. A novel adenosine triphosphate analog with a heavy atom to target the nucleotide binding site of proteins. *Protein Science*, 1995, 4, 1824-1831.

6a. Correll, C. C.; Freeborn, B.; Moore, P. B.; Steitz, T. A., "Metals, motifs, and recognition in the crystal structure of a 5S rLNA domain", *Cell* 1997, 91, 705-712.

7. Hendrickson, W. A; Ogata, C. M. Phase Determination from Multiwavenlength Anomalous Diffraction Measurements. *Methods in Enzymology, Part A,* 1997, 276, 494-523.

7a. Holbrook, S. R.; Kim, S.-H., "RNA Crystallography", *Biopolymers* 1997, 44, 3-21.

8. Hendrickson, W. A.; Pahler, A.; Smith, J. L.; Satow, Y.; Merritt, E. A.; Phizackerley, R. P. Crystal structure of core streptavidin determined from multiwavelength anomalous diffraction of synchrotron radiation. *Proc. Natl. Acad. Sci. USA* 1989, 86, 2190-2194.

8a. Kim, R.; Holbrook, E. L.; Jancarik, J.; Pandit, J.; Weng X.; Bohm, A.; Kim, S.-H., "High-Resolution Crystals and Preliminary X-ray Diffraction Studies of a Catalytic RNA", *Acta Cryst.* 1994, D50, 290-292.

9. Yang, W.; Hendrickson, W. A.; Crouch, R. J.; Satow, Y. Structure of ribonuclease H phased at 2 A resolution by MAD analysis of the selenomethionyl protein. *Science* 1990, 249, 1398-1405.

9a. Derivative of the crystal in Reference 8 (diffraction resolution, 2.4 A) has not yet been prepared; all trials failed, including halogen derivatives. (personal communication with S. Holbrook in June, 2000).

10. Ferre-D'Amare, A. R.; Zhou, Kaihong; Doudna, J. A. Crystal structure of a hepatitis delta virus ribozyme. *Nature,* 1998, 395, 567-574.

10a. Willis, M. C.; Hicke, B. J.; Uhlenbeck, O. C.; Cech, T. R.; Koch, T. H., "Photocrosslinking of 5-iodouracil-substituted RNA and DNA to proteins", *Science* 1993, 262, 1255-1257.

11. Hale, K. J.; Manaviazar, S, Novel Pyranoid Glycals Derived from D-Fructose. *Tetrahedron Lett.* 1994, 35, 8873-8876.

11a. Personal communication with M. Egli, in February 2000.

12. Kawashima, E.; Toyama, K.; Ohshima, K.; Kainosho, M.; Kyogoku, Y.; Ishido, Y. Novel synthesis of 2'-deoxy[5'-$^2$H] ribonucleosides derivatives from 5'-O—Ac-2'-deoxy-5'-PhSe-ribonucleoside derivatives. *Tetrahedron Lett.* 1995, 36, 6699-6700.

12a. Hendrickson, W. A.; Pahler, A.; Smith, J. L.; Satow, Y.; Merritt, E. A.; Phizackerley, R. P., "Crystal structure of core streptavidin determined from multiwavelength anomalous diffraction of synchrotron radiation", *Proc. Natl. Acad. Sci. USA* 1989, 86, 2190-2194.

13. Andreadou, I.; Menge, W. M. P. B.; Commandeur, J. N. M.; Worthington, E. A.; Vermeulen, N. P. E. Synthesis of Novel Se-Substituted Selenocysteine Derivatives as Potential Kidney Selective Prodrugs of Biologically Active Selenol Compounds: Evaluation of Kinetics of Elimination Reactions in Rat Renal Cytosol. *J. Med. Chem.* 1996, 39, 2040-2046.

13a. Yang, W.; Hendrickson, W. A.; Crouch, R. J.; Satow, Y., "Structure of ribonuclease H phased at 2 A resolution by MAD analysis of the selenomethionyl protein", *Science* 1990, 249, 1398-1405.

14. Mautner, H. C. The synthesis and properties of some selenopurines and selenopyrimidines. *J. Am. Chem. Soc.* 1956, 78, 5292-5294.

14a. Hendrickson, W. A.; Ogata, C. M., "Phase Determination from Multiwavelength Anomalous Diffraction Measurements", *Methods in Enzymology,* 1997, 276, 494-523.

15. Richert, C.; Roughton, A. L.; Benner, A. S. Nonionic Analogs of RNA with Dimethylene Sulfone Bridges. *J. Am. Chem. Soc.* 1996, 118, 4518-4531.

15a. Carrasco, N.; Ginsburg, D.; Huang, Z., "Synthesis of Selenium-Derivatized Nucleosides and Triphosphates", manuscript submitted.

16. Huang, Z.; Schneider, K. C.; Benner, S. A. Building blocks for oligonucleotide analogues with Dimethylene sulfide, sulfoxide, and sulfone groups replacing phosphodiester linkages. *J. Org. Chem.* 1991, 56, 3869-3882.

16a. Carrasco, N.; Du, Q.; Huang, Z., "Synthesis of Selenium-Derivatized Oligonucleotides for X-ray Crystallography", manuscript in preparation.

17. Jakiwczyk, O. M.; Kristoff, E. M.; McPhee, D. Convenient preparation of dialkyl diselenides: a large scale synthesis of bis-(2-hydroxyethyl)diselenide. *Synthetic Communication* 1993, 23, 195-199.

17a. Ferre-D'Amare, A. R.; Zhou, K; Doudna, J. A., "Crystal structure of a hepatitis delta virus ribozyme", *Nature,* 1998, 395, 567-574.

18. Tang, X.-Q.; Liao, X.; Piccirilli, J. A. 2'-C-Branched Ribonucleosides: Synthesis of the Phosphoramidite Derivatives of 2'-C-Methylcytidine and Their Incorporation into Oligonucleotides. *J. Org. Chem.* 1999, 64, 747-754.

18a. Mishra, N. C.; Broom, A. D., "A Novel Synthesis of Nucleoside 5'-Triphosphates", *J. Chem. Soc., Chem. Commun.* 1991, 1276-1277.

19. Richert, C.; Roughton, A. L.; Benner, S. A., "Nonionic Analogs of RNA with Dimethylene Sulfone Bridges", *J. Am. Chem. Soc.,* 1996, 118, 4518-4531.

20. Chechik, V.; Zhao, M.; Crooks, R. M., Self-Assembled Inverted Micelles Prepared from a Dendrimer Template: Phase Transfer of Encapsulated Guests, J. Am. Chem. Soc. 1999, 121, 4910-4911.

21. Jankowska, J.; Sobkowska, A.; Cieslak, J.; Sobkowski, M.; Kraszewski, A.; Stawinski, J.; Shugar, D. *J. Org. Chem.* 1998, 63, 8150-8156.

22. Mori, K.; Boiziau, C.; Cazenave, C.; Matsukura, M.; Subasinghe, C.; Cohen, J. S.; Broder, S.; Toulme, J. J.; Stein, C. A., "Phosphoroselenoate oligodeoxynucleotides: synthesis, physico-chemical characterization, anti-sense inhibitory properties and anti-HIV activity", *Nucl. Acids. Res.* 1989 17, 8207-8219.
23. Stawiski, J.; Thelin, M., "3H-1,2-benzothiaselenol-3-one. A new selenizing reagent for nucleoside H-phosphonate and H-phosphonothioate diesters", *J. Org. Chem.* 1994, 59, 130-136.
24. a). Hoard, D. E.; Ott, D. G., "Coversion of mono- and oligodeoxyribonucleotides to 5'-triphosphates", *J. Am. Chem. Soc.* 1965, 87, 1785-1788; b) Secrist III, J. A.; Tiwari, K. N.; Shortnacy-Fowler, A. T.; Messini, L.; Riordan, J. M.; Montgomery, J. A.; Meyers S. C.; Ealick, S. E., "Synthesis and Biological Activity of Certain 4'-Thio-D-arabinofuranosylpurine Nucleosides", *J. Med. Chem.*, 1998, 41, 3865-3871; c) Zhen Huang, K. Christian Schneider, and Steven A. Benner, "Building Blocks for Oligonucleotide Analogs with Dimethylene Sulfide, Sulfoxide, and Sulfone Groups Replacing Phosphodiester Linkages", *J. Org. Chem.,* 1991, Vol. 56, 3869-3882.
25. Smith, J. S.; Nikonowicz, E. P., "Phosphorothioate substitution can substantially alter RNA conformation", *Biochemistry* 2000, 39, 5642-5652.
26. Dunbar, D. A.; Wormsley, S.; Lowe T. M.; Baserga, S. J., "Fibrillarin-associated box C/I) small nucleolar RNAs in *Trypanosoma brucei*. Sequence conservation and implications for 2'-O-ribose methylation of rRNA", *J Biol Chem* 2000, 275, 14767-14776.
27. Tereshko, V.; Portmann, S.; Tay, E. C.; Martin, P.; Natt, F.; Altmann, K.-H.; Egli, M., "Correlating structure and stability of DNA duplexes with incorporated 2'-O-modified RNA analogues", *Biochemistry* 1998, 37, 10626-10634.
28. Personal communication with Martin Egli.
29. Rubin, J.; Brennan, T; Sundaralingam, M., "Crystal and molecular structure of a naturally occurring dinucleoside monophosphate. Uridylyl-(3'-5')-adenosine hemihydrate. Conformational "rigidity" of the nucleotide unit and models for polynucleotide chain folding", *Biochemistry* 1972, 11, 3112-3118.
30. Jain, S. C.; Zon, G.; Sundaralingam, M., "Base only binding of spermine in the deep groove of the A-DNA octamer d(GTGTACAC)." *Biochemistry* 1989, 28, 2360-2364.
31. Scott, W. G.; Finch, J. T.; King, A., "The crystal structure of an all-RNA hammerhead ribozyme: a proposed mechanism for RNA catalytic cleavage", *Cell,* 1995, 81, 991-1002.
32. Scott, W. G.; Murray, J. B.; Arnold, J. R. P.; Stoddard, B. L.; Klug, A., "Capturing the structure of a catalytic RNA intermediate: the hammerhead ribozyme", *Science* 1996, 274, 2065-2069.
33. Huang, Z.; Szostak, J. W., "A simple method for 3'-labeling of RNA", Nucleic Acids Research 1996, 24, 4360-4361.
34. Kim, R.; Holbrook, E. L.; Jancarik, J.; Kim, S.-H., "Synthesis and purification of milligram quantities of short RNA transcripts", *BioTechniques* 1995, 18, 992-994.
35. Moore, M. J.; Sharp, P. A., "Site-specific modification of pre-mRNA: the 2'-hydroxyl groups at the splice sites", *Science* 1992, 256, 992-997.
36. Biswas, R.; Mitra, S, N.; Sundaralingam, M., "0.76 A structure of a pyrimidine start alternating A-RNA hexamer r(CGUAC)dG", *Acta Crystallogr., Sect. D,* 1998, 54, 570-576.
37. Camerman, N.; Fawcett, J. K.; Camerman, A., "Molecular structure of a deoxyribose-dinucleotide, sodium thymidylyl-(5' yields to 3')-thymidylate-(5') hydrate (pTpT), and a possible structural model for polythymidylate", *J. Mol. Biol.,* 1976, 107, 601-621.
38. Vijay-Kumar, S.; Sakore, T. D.; Sobell, H. M., "Structure of a novel drug-nucleic acid crystalline complex: 1,10-phenanthroline-platinum (11) ethylenediamine-5'-phosphoryl-thymidylyl(3'-5') deoxyadenosine", *J. Biomol. Struct. Dyn.,* 1984, 2, 333-344.
39. Takusagawa, F; Dabrow, M.; Neidle, S.; Berman, H. M., "The structure of a pseudo intercalated complex between actinomycin and the DNA binding sequence d(GpC)", *Nature* 1982, 296, 466-469.
40. Egli, M.; Minasov, G., "Recent Advances in RNA Crystallography". In Book "Ribozymes, Biochemistry and Biotechnology". Krupp, G.; Gaur, R. K., Eds., 2000, in press.

What is claimed is:

1. A selenium-containing compound having the structure of formula I:

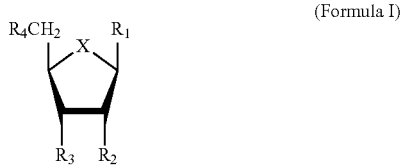

(Formula I)

wherein:
- (a) $R_1$ is a nucleic acid base selected from the group consisting of adenine, 8-selenoadenine, guanine, 6-selenoguanine, and 8-selenoguanine, or is a protected nucleic acid base selected from the group consisting of protected adenine, 8-selenoadenine, guanine, 6-selenoguanine, and 8-selenoguanine;
- (b) $R_2$ is H, HO, alkyl-O, TBDMS-O, TOM-O group, ACE-O group, orthoester group, diselenide, or alkyl-Se;
- (c) $R_3$ is H, HO, alkyl-O, TBDMS-O, diselenide, alkyl-Se, phosphoramidite, phosphoroselenoamidite, phosphate, a 5' linked nucleotide, a 5' linked seleno-nucleotide, a 5' linked oligonucleotide, a 5' linked seleno-oligonucleotide, a 5' linked nucleic acid chain, or a 5' linked seleno-nucleic acid chain, wherein any phosphorus atom of a bridging phosphate of the 5' linked seleno-nucleotide, the 5' linked seleno-oligonucleotide, or the 5' linked seleno-nucleic acid chain is bonded to non-selenium atoms;
- (d) $R_4$ is H, HSe, diselenide, alkyl-Se, alkyl-O, DMTr-O, TBDMS-O, (alkyl-O)$_3$Si-O, phosphate, diphosphate, diphosphoroselenoate, triphosphate, or triphosphoroselenoate, a 3' linked nucleotide, a 3' linked seleno-nucleotide, a 3' linked oligonucleotide, a 3' linked seleno-oligonucleotide, a 3' linked nucleic acid chain, or a 3' linked seleno-nucleic acid chain, wherein any phosphorus atom of a bridging phosphate of the 3' linked seleno-nucleotide, the 3' linked seleno-oligonucleotide, or the 3' linked seleno-nucleic acid chain is bonded to non-selenium atoms; and
- (e) X is an oxygen atom or a selenium atom;

wherein at least one of $R_1$, $R_2$, or X comprises at least one selenium atom, and wherein alkyl is a saturated or unsaturated, branched or unbranched hydrocarbon group having between 1 and 24 carbon atoms.

2. A selenium-containing compound according to claim 1, wherein:
- (a) $R_1$ is a nucleic acid base selected from the group consisting of adenine, 8-selenoadenine, guanine, 6-selenoguanine, and 8-selenoguanine; or is a protected nucleic acid base selected from the group consisting of protected adenine, 8-selenoadenine, guanine, 6-selenoguanine, and 8-selenoguanine;
- (b) $R_2$ is H, HO, alkyl-O, TBDMS-O, TOM-O group, ACE-O group, methyl-Se, ethyl-Se, or propyl-Se;
- (c) $R_3$ is H, HO, alkyl-O, TBDMS-O, methyl-Se, ethyl-Se, propyl-Se, phosphoramidite, or phosphate;
- (d) $R_4$ is H, alkyl-O, DMTr-O, methyl-Se, ethyl-Se, propyl-Se, phosphate, diphosphate, diphosphoroselenoate, triphosphate, or triphosphoroselenoate; and
- (e) X is an oxygen atom wherein at least one of $R_1$ or $R_2$ comprises at least one selenium atom.

3. A selenium-containing compound according to claim 1, wherein:
- (a) $R_1$ is a nucleic acid base selected from the group consisting of adenine, 8-selenoadenine, guanine, 6-selenoguanine, and 8-selenoguanine; or is a protected nucleic acid base selected from the group consisting of protected adenine, 8-selenoadenine, guanine, 6-selenoguanine, and 8-selenoguanine;
- (b) $R_2$ is H, alkyl-O, TBDMS-O, TOM-O group, ACE-O group, methyl-Se, ethyl-Se, or propyl-Se;
- (c) $R_3$ is phosphoramidite;
- (d) $R_4$ is DMTr-O; and
- (e) X is an oxygen atom;

wherein at least one of $R_1$ or $R_2$ comprises at least one selenium atom.

4. A selenium-containing compound according to claim 1, wherein:
- (a) $R_1$ is a nucleic acid base selected from the group consisting of adenine and guanine; or is a protected nucleic acid base selected from the group consisting of protected adenine and guanine;

(b) $R_2$ is methyl-Se;
(c) $R_3$ is phosphoramidite;
(d) $R_4$ is DMTr-O, TBDMS-O, or (alkyl-O)$_3$Si—O; and
(e) X is an oxygen atom.

5. A selenium-containing compound according to claim 1, wherein:
   (a) $R_1$ is a protected nucleic acid base selected from the group consisting of protected 8-selenoadenine, 6-selenoguanine, and 8-selenoguanine;
   (b) $R_2$ is H, alkyl-O, TBDMS-O, TOM-O group, or ACE-O group;
   (c) $R_3$ is phosphoramidite;
   (d) $R_4$ is DMTr-O; and
   (e) X is an oxygen atom.

6. A selenium-containing compound according to claim 1, wherein:
   (a) $R_1$ is a nucleic acid base selected from the group consisting of adenine and guanine;
   (b) $R_2$ is diselenide or alkyl-Se;
   (c) $R_3$ is HO or H;
   (d) $R_4$ is H; and
   (e) X is an oxygen atom.

7. A selenium-containing compound according to claim 1, wherein:
   (a) $R_1$ is a nucleic acid base selected from the group consisting of adenine and guanine;
   (b) is HO or H;
   (c) $R_3$ is diselenide or alkyl-Se;
   (d) $R_4$ is H; and
   (e) X is an oxygen atom.

8. A selenium-containing compound according to claim 1, wherein:
   (a) $R_1$ is a nucleic acid base selected from the group consisting of 8-selenoadenine, 6-selenoguanine, and 8-selenoguanine;
   (b) $R_2$ is HO or H;
   (c) $R_3$ is HO or H;
   (d) $R_4$ is H; and
   (e) X is an oxygen atom.

9. A selenium-containing compound according to claim 1, wherein:
   (a) $R_1$ is a nucleic acid base selected from the group consisting of adenine, 8-selenoadenine, guanine, 6-selenoguanine, and 8-selenoguanine;
   (b) $R_2$ is H, HO, or methyl-Se;
   (c) $R_3$ is H, HO, or methyl-Se;
   (d) $R_4$ is phosphate, diphosphate, diphosphoroselenoate, triphosphate, or triphosphoroselenoate; and
   (e) X is an oxygen atom;
   wherein at least one of $R_1$, or $R_2$ comprises at least one selenium atom.

10. A selenium-containing compound according to claim 1, wherein:
    (a) $R_1$ is a nucleic acid base selected from the group consisting of 8-selenoadenine, 6-selenoguanine, and 8-selenoguanine;
    (b) $R_2$ is H or HO;
    (c) $R_3$ is HO;
    (d) $R_4$ is triphosphate; and
    (e) X is an oxygen atom.

11. A process for preparing a compound having the structure of formula I:

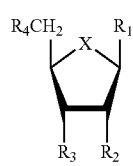

(Formula I)

wherein:
   (a) $R_1$ is a nucleic acid base selected from the group consisting of adenine, 8-selenoadenine, guanine, 6-selenoguanine, and 8-selenoguanine; or is a protected nucleic acid base selected from the group consisting of protected adenine, 8-selenoadenine, guanine, 6-selenoguanine, and 8-selenoguanine;
   (b) $R_2$ is H, HO, alkyl-O, TBDMS-O, TOM-O group, ACE-O group, orthoester group, diselenide, alkyl-Se, or $Z_1$;
   (c) $R_3$ is H, HO, alkyl-O, TBDMS-O, diselenide, alkyl-Se, phosphoramidite, phosphoroselenoamidite, phosphate, a 5' linked nucleotide, a 5' linked seleno-nucleotide, a 5' linked oligonucleotide, a 5' linked seleno-oligonucleotide, a 5' linked nucleic acid chain, or a 5' linked seleno-nucleic acid chain, or $Z_2$, wherein any phosphorus atom of a bridging phosphate of the 5' linked seleno-nucleotide, the 5' linked seleno-oligonucleotide, or the 5' linked seleno-nucleic acid chain is bonded to non-selenium atoms;
   (d) $R_4$ is H, HSe, diselenide, alkyl-Se, alkyl-O, DMTr-O, TBDMS-O, (alkyl-O)$_3$Si—O, phosphate, diphosphate, diphosphoroselenoate, triphosphate, or triphosphoroselenoate, a 3' linked nucleotide, a 3' linked seleno-nucleotide, a 3' linked oligonucleotide, a 3' linked seleno-oligonucleotide, a 3' linked nucleic acid chain, a 3' linked seleno-nucleic acid chain, or $Z_3$, wherein any phosphorus atom of a bridging phosphate of the 3' linked seleno-nucleotide, the 3' linked seleno-oligonucleotide, or the 3' linked seleno-nucleic acid chain is bonded to non-selenium atoms; and
   (e) X is an oxygen atom or a selenium atom;
wherein at least one of $R_1$, $R_2$, or X comprises at least one selenium atom; and wherein $Z_1$, $Z_2$, or $Z_3$ is diselenide, alkyl-Se, or phosphoroselenoamidite; wherein alkyl is a saturated or unsaturated, branched or unbranched hydrocarbon group having between 1 and 24 carbon atoms; and wherein at least one of $R_2$, $R_3$, or $R_4$ is $Z_1$, $Z_2$, or $Z_3$;
   the process comprising:
   providing a precursor, the precursor having the structure of the compound except that $Z_1$, $Z_2$, or $Z_3$ is a leaving group; and reacting the precursor with a selenide ion, a diselenide ion, or an alkyl selenide ion; wherein the reaction occurs in a two phase system comprising a water-immiscible organic phase and an aqueous phase in the presence of a phase transfer catalyst, wherein the phase transfer catalyst causes selenide ion or alkyl selenide ion transfer between the water-immiscible organic phase and the aqueous phase; or in one phase of an organic solvent, or a mix of solvents.

12. A process according to claim 11, wherein:
   (a) $R_1$ is a nucleic acid base selected from the group consisting of adenine, 8-selenoadenine, guanine, 6-selenoguanine, and 8-selenoguanine; or is a protected nucleic acid base selected from the group consisting of protected adenine, 8-selenoadenine, guanine, 6-selenoguanine, and 8-selenoguanine;
(b) $R_2$ is H, HO, alkyl-O, TBDMS-O, TOM-O group, ACE-O group, methyl-Se, ethyl-Se, or propyl-Se;
(c) $R_3$ is H, HO, alkyl-O, TBDMS-O, methyl-Se, ethyl-Se, propyl-Se, phosphoramidite, or phosphate;
(d) $R_4$ is H, alkyl-O, DMTr-O, methyl-Se, ethyl-Se, propyl-Se, phosphate, diphosphate, diphosphoroselenoate, triphosphate, or triphosphoroselenoate; and
(e) X is an oxygen atom;
wherein at least one of $R^1$ or $R_2$ comprises at least one selenium atom.

13. A process according to claim 11, wherein:
(a) $R_1$ is a nucleic acid base selected from the group consisting of adenine, 8-selenoadenine, guanine, 6-selenoguanine, and 8-selenoguanine; or is a protected nucleic acid base selected from the group consisting of protected adenine, 8-selenoadenine, guanine, 6-selenoguanine, and 8-selenoguanine;
(b) $R_2$ is H, alkyl-O, TBDMS-O, TOM-O group, ACE-O group, methyl-Se, ethyl-Se, or propyl-Se;
(c) $R_3$ is phosphoramidite;
(d) $R_4$ is DMTr-O; and
(e) X is an oxygen atom;
wherein at least one of $R_1$ or $R_2$ comprises at least one selenium atom.

14. A process according to claim 11, wherein the water immiscible organic phase comprises toluene, benzene, or hexane.

15. A process according to claim 11, wherein the phase transfer catalyst comprises a quaternary ammonium ion and a counterion.

16. A process according to claim 11, wherein the phase transfer catalyst comprises a quaternary ammonium ion and a counterion selected from $F^-$, $Cl^-$, $Br^-$, $I^-$, $ClO_3^-$, $NO_3^-$, $HCO_3^-$ and $HSO_4^-$.

17. A process according to claim 11, wherein an organic solvent for one phase reaction is ethanol, DMF, acetonitrile, or a mix of solvents.

* * * * *